(12) United States Patent
Gurewitsch et al.

(10) Patent No.: US 8,060,195 B2
(45) Date of Patent: Nov. 15, 2011

(54) DEVICES, SYSTEMS AND METHODS FOR BIOIMPEDANCE MEASUREMENT OF CERVICAL TISSUE AND METHODS FOR DIAGNOSIS AND TREATMENT OF HUMAN CERVIX

(75) Inventors: Edith D. Gurewitsch, Baltimore, MD (US); Melanie Ruffner, Pittsburgh, PA (US); Kenny H. Ching, Singapore (SG); Somponnat Sampattavanich, Cambridge, MA (US); Ashkon Shaahinfar, Woodbridge, CA (US); Yen S. Hoe, Singapore (SG); Elbert S. Hu, San Francisco, CA (US)

(73) Assignee: The Johns Hopkins University, Baltimore, MD (US)

( * ) Notice: Subject to any disclaimer, the term of this patent is extended or adjusted under 35 U.S.C. 154(b) by 1017 days.

(21) Appl. No.: 10/555,503

(22) PCT Filed: May 3, 2004

(86) PCT No.: PCT/US2004/013720
§ 371 (c)(1),
(2), (4) Date: Nov. 26, 2008

(87) PCT Pub. No.: WO2004/098389
PCT Pub. Date: Nov. 18, 2004

(65) Prior Publication Data
US 2009/0171234 A1    Jul. 2, 2009

Related U.S. Application Data

(60) Provisional application No. 60/497,300, filed on Aug. 22, 2003, provisional application No. 60/467,456, filed on May 2, 2003.

(51) Int. Cl.
*A61B 5/00* (2006.01)
*A61B 5/05* (2006.01)
*A61B 5/103* (2006.01)
*A61B 5/117* (2006.01)

(52) U.S. Cl. .............. 600/547; 600/304; 600/591

(58) Field of Classification Search .......... 600/304, 600/372, 373, 376, 393, 547, 551, 591; 607/138
See application file for complete search history.

(56) References Cited

U.S. PATENT DOCUMENTS
4,577,640 A    3/1986    Hofmeister
(Continued)

FOREIGN PATENT DOCUMENTS
DE    41 00 568 A1    7/1992
(Continued)

OTHER PUBLICATIONS

Jossinet et al., "Quantitative Technique for Bio-Electrical Spectroscopy," Journal of Biomedical Engineering, Butterworth, Guildford, GB, vol. 7, No. 4, Oct. 1, 1985, pp. 289-294.

*Primary Examiner* — Max Hindenburg
*Assistant Examiner* — Jonathan M Foreman
(74) *Attorney, Agent, or Firm* — Edwards Angell Palmer & Dodge LLP; Peter F. Corless; William J. Daley, Jr.

(57) ABSTRACT

Featured are apparatuses for measuring bioimpendence of tissues of the cervix, more specifically the mammalian cervix. Also featured are methods for examining the tissues of the cervix for clinical or diagnostic purposes such as during routine gynecological examinations to determine early onset of labor in pregnant patients or to assess such tissues for the presence of abnormalities such as cancerous lesions in both pregnant and non-pregnant women. Also featured are methods for treating onset of early or pre-term labor that embody such devices, apparatuses and methods of the present invention. Also featured are systems embodying such devices, apparatuses and/or methods, where such systems preferably are configured to provide diagnostic and/or clinical information to further assist the diagnostician or clinician in diagnosing and/or examining pregnant or non-pregnant patients.

49 Claims, 17 Drawing Sheets

U.S. PATENT DOCUMENTS

| | | | |
|---|---|---|---|
| 5,068,619 A | 11/1991 | Nakano et al. | |
| 5,199,442 A * | 4/1993 | Seager et al. | 607/138 |
| 6,026,323 A | 2/2000 | Skladnev et al. | |
| 6,169,914 B1 | 1/2001 | Hovland et al. | |
| 6,270,458 B1 | 8/2001 | Barnea | |
| 2003/0060696 A1 | 3/2003 | Skladnev et al. | |
| 2003/0105411 A1 | 6/2003 | Smallwood et al. | |

FOREIGN PATENT DOCUMENTS

| | | |
|---|---|---|
| EP | 1 385 436 A2 | 1/2004 |
| JP | 01-113645 A | 5/1989 |
| WO | WO-00/19894 | 4/2000 |
| WO | WO-01/67098 A1 | 9/2001 |
| WO | WO-2005/096707 A2 | 10/2005 |

* cited by examiner

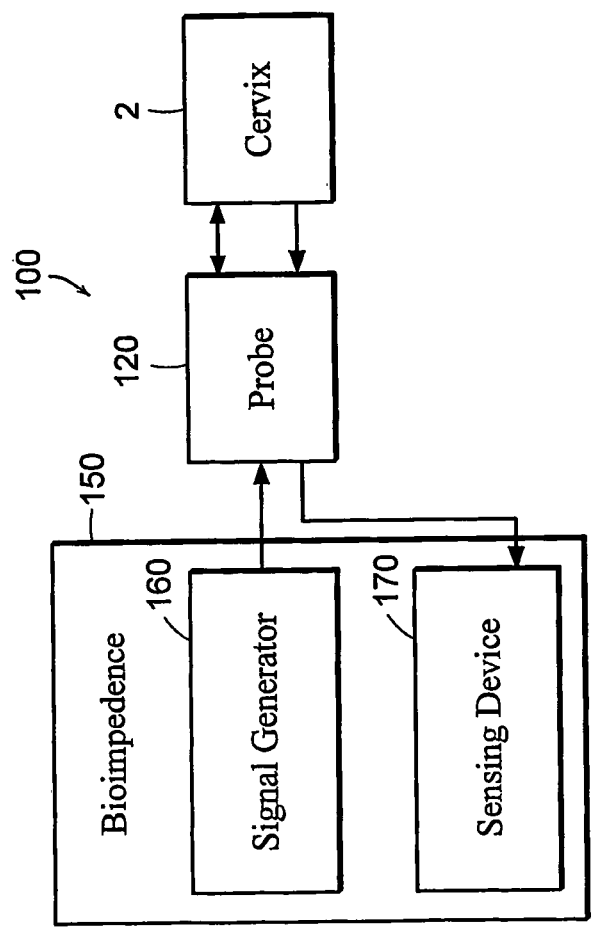
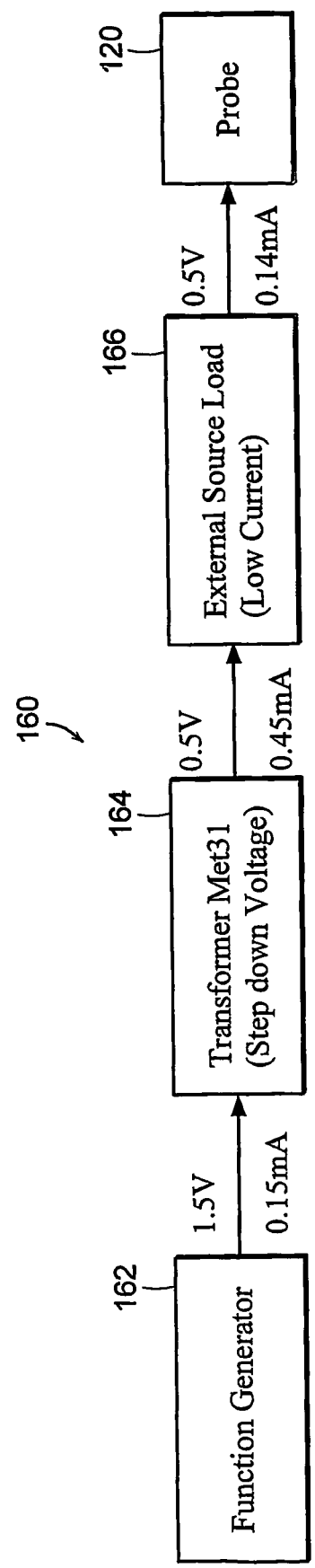
FIG. 2A
FIG. 2B

Van Der Pauw Method $$p = \frac{\pi \cdot d}{\ln 2} \cdot \frac{(R_{BD,AC} - R_{BC,DA})}{2} \cdot f\left(\frac{R_{AB,CD}}{R_{BC,DA}}\right)$$

$$\mu H = \frac{d}{B} \cdot \frac{\Delta R_{BD,AC}}{p} \qquad R_{AB,CD} = \frac{\vartheta D - \vartheta C}{I R_{AB}}$$

DEVICES, SYSTEMS AND METHODS FOR BIOIMPEDANCE MEASUREMENT OF CERVICAL TISSUE AND METHODS FOR DIAGNOSIS AND TREATMENT OF HUMAN CERVIX

This application claims the benefit of U.S. Provisional Application Ser. No. 60/467,456 filed May 2, 2003 and U.S. Provisional Application Ser. No. 60/497,300 filed Aug. 22, 2003, the teachings of all are incorporated herein by reference.

FIELD OF INVENTION

The present invention relates to devices, systems and methods for measuring bioimpedance, more specifically bioimpedance of the human cervix and the present invention also relates to methods that embody such measuring methods for diagnosis, examination and treatment of tissue and/or organs, more specifically the human cervix and tissue of the human cervix.

BACKGROUND OF THE INVENTION

Pre-term labor or pre-term birth is a significant problem that costs billions of health care dollars annually. An infant is considered pre-term if born before thirty-seven weeks of gestation. Of the estimated 6,250,000 pregnancies that occur in the U.S. each year, about 11% are pre-term births. *Obstetrics-Normal and Problem Pregnancies*, 4th ed., Copyright® 2002 Churchill Livingstone, Inc. p. 755-763; http://www-.wvdhr.org/bph/hp2010/objective/16.htm, May 14, 2003. The use of reproductive technology, the increasing number of pregnancies for women over age of thirty-five, and the growing incidence of multiple births potentially can lead to future increases in this percentage. Furthermore, about 80% of the pre-term births occur spontaneously, while the remainder are induced in response to complications discovered with the fetus or mother. Mattison, D. R.; et al., *Pre-term Delivery: a public health perspective*, Paediatric and Perinatal Epidemology 2001, 15 (Supple. 2), 7-16.

Infants born pre-term are considerably less physiologically developed than normal term infants. Consequently and as illustrated in FIGS. 1A,B, especially high rates of acute newborn morbidity and mortality are associated with such infants, especially those born extremely pre-term (e.g., 23-27 weeks). These pre-term neonates also face greater risks for long term health problems than infants born full term. Such health problems include underdeveloped respiratory systems, complications to the nervous system, problems feeding, mental retardation, and intraventricular (brain) hemorrhage. *Confronting Pre-term Delivery in the 21st Century: From Molecular Intervention to Community Action* http://www.medscape.com/viewaarticle/408935. About 60% of all serious prenatal complications or deaths that occur are due to pre-term delivery. Further, pre-term birth also has been associated with several maternal complications including infection due to pre-term rupture of the membrane (PROM) and postpartum depression. The most significant source of maternal risk is associated with the higher rates of caesarean delivery. Premature delivery complicates the level of surgery required which increases the possibility of hemorrhage, thromboembolism and infection.

Pre-term births result not only in high medical risks but also result in higher medical costs, where the major medical costs are typically incurred after delivery. These pre-term newborn infants usually require a much longer hospital stay (e.g., the average hospital stay pf a pre-term infant is 21.7 days) and more expensive treatments than a normal term baby. Such treatments include incubation, respiratory assistance and dialysis. It has been reported that the cost for the care of premature infants is over six billion dollars annually, where about seventy five percent of this value is spent in the first year of life, mostly on the initial hospitalization. Studies to quantify such expenditures also show an inverse correlation between mean cost per surviving infant and the gestational age. As illustration, while a healthy pregnancy costs on average $6,400, the medical costs associated with a pre-term baby can cost $20,000 to $1 million, where the mean cost per infant for infants born between weeks 26-28 is about $49,000.

There are many conditions that may result in pre-term delivery. These include: genetic predisposition, maternal or fetal stress or infection, premature rupture of the amniotic membrane, abnormal hormonal signals, and abnormal uterine properties. Regardless of cause, the softening, dilation, and effacement of the cervix during pregnancy and labor do not occur as a result of uterine contractions alone, but are also a result of an active remodeling of the structure of the cervix. Pre-term labor is often a result of improper timing of the normal signals that trigger cervical remodeling, and pre-term softening of the cervical tissue can result in spontaneous abortion, pre-term delivery, and sometimes impairs normal vaginal delivery.

Regardless of the point during gestation that hormonal signals to remodel arrive, it is believed that they trigger similar changes in the cervix. In the transition to labor, the tissue of the human pregnant cervix undergoes significant remodeling, such that its predominantly collagen matrix is replaced by glycosaminoglycans. As a result of this "ripening," the cervix softens, thereby preparing for the thinning and dilation that will ultimately be required to allow the fetus to exit the womb.

If detected early enough, there are several treatments that may be very effective in delaying labor until an acceptable gestational age and level of fetal development occurs. These treatments vary from something as simple as bed rest to drugs that can be administered in an effort to postpone labor or arrest its progression. Such drugs include, but are not limited to beta-adrenergic receptor agonists, magnesium sulfate, calcium channel blockers, cyclooxygenase inhibitors, salbumatol, lidocaine and nitric oxide/nitric oxide donors. Corticosteriods also are frequently employed as a specific treatment to the premature fetus to enhance organ maturation as well as improving fetal lung function by speeding development of the lungs and respiratory enzymes necessary for oxygen transfer. These also may decrease the risk of intraventricualar hemorrhage and injury to the gastrointestinal tract. These treatments are more likely to be effective and safe if the onset of pre-term labor is caught early in the gestation period.

Accurate and early diagnosis of pre-term labor is a major problem as up to about 50% of patients being diagnosed with pre-term labor do not actually have pre-term labor and yet as many as 20% of symptomatic patients diagnosed as not being in labor will deliver prematurely. Such misdiagnosis is problematic because, as indicated herein, intervention early in the gestation period is more advantageous to effectively prevent pre-term delivery. Currently, a physician weighs the importance of several parameters such as patient history, biochemical test results, and examination of the cervix, to predict the onset of pre-term labor. For example, a patient history significant for certain obstetrical conditions, such as cervical incompetence, infections of the amniotic fluid, previous abortion or prior pre-term delivery has been shown to increase the risk of pre-term labor in an index or subsequent pregnancy.

The most reliable method of labor prediction involves the obstetrician to digitally palpitating (using his/her finger(s)) the cervix to evaluate its softness. Such examinations can be conducted in 1 to 2 hour intervals until the obstetrician is satisfied that progressive change in the consistency, position, dilation and effacement of the cervix is or is not occurring. This method, in addition to being dependent upon the experience of the obstetrician, is qualitative in nature and therefore large changes in cervical consistency must occur before a changes able to be felt. Obstetricians also can use ultrasound technology to determine the position of the fetus and the length of the cervix, but his data alone is not sufficient to predict whether delivery will occur.

The current absence of diagnostic methods that have acceptable rates of sensitivity and specificity has prompted researchers and others to look for other ways to predict pre-term labor earlier. Many of these methods are based on qualitatively measuring the physical changes, as opposed to biochemical ones, that have been discovered to occur in a cervix of a pregnant woman. More advanced diagnostic methods including transabdominal electromyography (EMG) and transvaginal ultrasound (TVS) do exist and have been shown to slightly increase diagnostic accuracy. Cervical length and force of muscle contractions are examples of how TVS and transabdominal EMG measure physical changes. TVS measures the cervical length using ultrasound wave resonance, which may reflect cervical incompetence. Unfortunately this method does have a number of disadvantages including uncertainty related to the lack of a standard cervical measurement to judge against and variations in cervical length due to filing of the bladder. Another technology that has been used to detect pre-term labor is transabdominal EMG that essentially involves measuring the voltage produced by uterine contractions. The main disadvantage concerning the use of this technique is that childbirth specific uterine contractions tend to occur relatively close to the time of actual delivery (e.g., about 4 days in advance). This, as a practical matter, is much to short for any preventive treatment to have a significant effect on the mother.

Despite the foregoing, it also should be recognized that despite about two decades of improvement in regards to neonatal care, the rate of pre-term birth over that time has not been reduced and has remained essentially at a annual rate of about 11%. Although many reasons for this abound, a significant issue as referred to herein is that by the time the onset of premature labor is recognized clinically, little is available to arrest the process. As such, it is desirous to be able to detect the onset of premature labor well it would become clinically apparent using conventional techniques. This would allow medical intervention to occur earlier in the gestation period than is possible presently and can increase the likelihood that such medical intervention can be more successful in delaying or preventing pre-term delivery as compared to what is possible using existing techniques.

Recently, the focus of a number of studies has been on using biochemical markers as indicators or pre-term labor. Certain concentrations of compounds, such as fetal fibronectin, placental protein, prolactin and estriol found in the serum or vaginal fluid/secretions of the mother would indicate a risk of pre-term delivery. These methods, are still highly experimental and also do not indicate with any certainty whether or not a particular patient will actually deliver pre-term.

In addition to early detection of pre-term labor, it also is desirous to assess the degree of cervical remodeling that can be used to determine the readiness or ripeness of the cervix for labor in general. This determination has important implications for choosing the method for inducing labor when indications to do so develop during the course of a complicated pregnancy. In addition, in the current age of cost containment, it also would be advantageous to have a mechanism by which one can more accurately predict the onset of labor even for pregnancies that go to normal term. This would allow for better planning and staffing of labor and delivery hospital units because anticipated volume of births could be more accurately predicted.

As a non-obstetrical application, it has been suggested that electrical impedance spectra of tissues, more specifically cervical tissue, might be useable as a screening technique for the detection of cervical precancers and more specifically a screening technique whereby there is good separation between normal and precancerous tissues. Brown et al., *Relation between tissue structure and imposed electrical current flow in certain neoplasia*, Lancet 2000, 335: 892-895. In the described technique a pencil probe with four flush mounted gold electrodes (i.e., mounted flush to face of the probe) was used to measure electrical impedance spectra from eight points on the cervix. The method and apparatus reported, however, was developed to determine the efficacy of the concept and thus are generally experimental in nature.

A comparative study of pregnant cervix and non-pregnant cervix using electrical impedance measurements also has been reported. O'Connel, M P; et al; *An in vivo comparative study of the pregnant and non-pregnant cervix using bioelectrical impedance measurements*, British Journal of Obstetrics and Gynecology, August 2000, Vol. 107, p. 1040-1041. The article postulates that the electrical impedance techniques could be used to characterize the changes in cervical hydration that precedes labor. The article also postulates that this may be of clinical value in the prediction of labor onset both term and pre-term.

In the described technique a pencil probe with four flush mounted gold electrodes (i.e., mounted flush to face of the probe) was used to measure electrical impedance spectra of the cervix. The study observed a resistivity difference between the tissues of the cervix of women in the delivery suite at the time of induction of labor prior to any intervention and the tissues of the cervix of non-pregnant women. The method and apparatus reported, however, was developed to determine the efficacy of the general concept that there was a noticeable difference between the electrical impedance measured for cervical tissues of women in the later stages of pregnancy and women that are not pregnant As to other described postulated clinical uses, the article merely postulates or suggests that electrical impedance might be useable for such uses but does not include a demonstration or disclosure of the use of a bioimpedance measurement technique for the other suggested and described clinical uses.

It thus would be desirable to provide non-invasive devices, apparatuses, systems and methods that allow a clinician or obstetrician to directly measure the electrical impedance of the cervical tissue of a patient so as to allow the clinician to assess the cervical tissue for obstetrical or non-obstetrical related diagnosis/examination. It would be particularly desirable to provide such a device apparatus, system and method that would allow a clinician to make a determination of the onset of pre term labor earlier in gestation as compared to prior art devices and/or techniques. It also would be desirable to provide systems embodying such devices and apparatuses whereby the measurements can be evaluated so further clinical information (e.g., an out of norm condition indication) is provided by the system to assist the clinician/diagnostician with the examination or diagnosis of a given patient. Such devices, apparatuses and systems preferably would be simple in construction and easy to use by the clinician, diagnostician, or obstetrician. Such devices, apparatuses and methods also preferably would have the beneficial effect of reducing the risk of neonatal mortality from pre-maturity, reducing the risk and/or amount of medical treatment needed for the pre-term infant, and reducing maternal risk. Such devices, apparatuses and methods also preferably would have the beneficial effect of reducing misdiagnosis particularly when compared with what occurs with the use of conventional obstetrical techniques for assessing cervical tissues and/or the risk for onset of pre-term delivery. Such devices, apparatuses, systems and methods also preferably are easily adaptable for use in combination with existing techniques and methods to assess the cervical tissues for non-obstetrical purposes so as to reduce the need to use invasive techniques for assessing cervical tissue (e.g., minimizing cervical biopsies).

SUMMARY OF THE INVENTION

The present invention features devices and apparatuses for measuring bioimpedance of tissues of the cervix, more specifically the mammalian cervix. Also featured are methods related thereto, more specifically methods for examining the tissues of the cervix for clinical or diagnostic purposes such as during routine gynecological examinations to determine early onset of labor in pregnant patients or to assess such tissues for the presence of abnormalities such as cancerous lesions in both pregnant and non-pregnant women. Also featured are methods for treating onset of early or pre-term labor or delivery, which methods embody such devices, apparatuses and methods of the present invention. Also featured are systems embodying such devices, apparatuses and/or methods of the present invention. Such systems preferably are configured and arranged so as to provide diagnostic and/or clinical information to further assist the diagnostician or clinician in diagnosing and/or examining pregnant or non-pregnant patients. Such diagnostic/clinical information is generated based on the bioimpedance measurements taken using such devices and apparatuses of the present invention and in more specific embodiments, is generated based on comparisons of the measured data with developed sets of data representing any one of a number of possible conditions of the cervical tissues being examined. Such devices, apparatus, systems and methods, including embodiments and aspects thereof, are discussed and described herein.

In its broadest aspects, the bioimpedance measuring apparatus of the present invention includes a bioimpedance measuring device and a signal generating/sensing device being operably coupled to the bioimpedance measuring device. The bioimpedance measuring device includes a tip member that is configured and arranged so as to include a plurality or more of electrodes at least an end of each being exposed so as to contact and be put into electrical contact with the cervical tissues. The bioimpedance measuring device further includes a shaft member to which the tip member is operably secured to an end of the shaft member. The shaft member is configured and arranged so the user can insert the tip member into an opening, natural or artificial, in the mammalian body (e.g., the vagina) and so the user can localize the tip member proximal to the tissues to be examined and put the electrodes in contact with such tissues by manipulation of the shaft member manually or mechanically.

In specific embodiments, the tip member includes a multiplicity of such electrodes that are arranged so portions of each electrode extend a predetermined distance outwardly from a surface of the tip member. In more specific embodiments, the tip member includes three or more electrodes, four or more electrodes, eight or more electrodes, or N×4 electrodes, where N is an integer. In further specific embodiments, the electrodes are arranged so as to form a plurality or more of radially arranged electrodes, so as to form one or more linear electrode arrays each linear array extending widthwise or radial across the tip member surface, or so as to form a non-linear array (e.g., a tetrahedral, rectilinear or circular) of electrodes on the tip surface.

In one particular illustrative embodiment, the tip member includes four or more electrodes, more specifically four electrodes that are arranged to form a line of electrodes that are spaced from each other and that extend across a width or radial of the tip member surface. In further embodiments, N linear electrode arrays are arranged and presented on the tip member surface, where N is an integer $\geq 2$. The N linear arrays are arranged so that one array is at an angle with respect to another of the arrays and more specifically so that a midpoint of each linear array is located and arranged so as to be in common (e.g., each linear array forms a radial about a common point of rotation). In a more specific embodiment, the tip member includes two linear arrays that are arranged on the tip member surface so the second array is orthogonal to the first array so as to essentially form a plurality of crossing linear electrodes.

In further embodiments, the electrodes of each linear array are arranged electrically so as to form a tetrapolar electrode configuration, such that two of the four electrodes form an electrical circuit when in contact with the tissues so as to allow signals or current from the signal generating/sensing device to flow through the tissue and such that the other of the two electrodes can sense a voltage or other electrical characteristic of the tissue when such signals or current is flowing through the tissue.

In yet further more specific embodiments, the predetermined distance for each of the four or more electrodes is controlled such that the electrodes are configured so as to extend from the top surface in a manner that generally mirrors the anatomical structure presented by the opposing cervical tissues. In more particular embodiments, the two electrodes innermost located in the linear array are configured and arranged so that each extend further from the tip surface than either of the two outboard electrodes of the linear array. In more specific embodiments, the pre-determined distance of the inner two electrodes is set such that the force applied on the tissues by the inner two electrodes is not substantially different than the force being applied on the tissues by the outer two electrodes.

In another particular illustrative embodiment, the tip member includes four or more electrodes, more specifically four electrodes, that array arranged so the electrodes essentially form a tetrahedral or rectilinear shape across the tip member surface. In further embodiments, the electrodes are arranged so as to form a square and so the electrodes are arranged electrically so as to form a square tetrapolar electrode configuration, such that at any time two of the four electrodes form an electrical circuit when in contact with the tissues so as to allow signals or current from the signal generating/sensing device to flow through the tissue and such that the other of the two electrodes also are electrically coupled to the signal generating/sensing device and so that the other of the two electrodes can sense a voltage or other electrical characteristic of the tissue when such signals or current is flowing through the tissue.

In yet another particular illustrative embodiment, the tip member includes three or more electrodes, more specifically three electrodes, that array arranged so the electrodes essentially form a circular electrode array. In more specific embodiments, the circular electrode array includes a centrally located circular electrode and a plurality of annular electrodes, more specifically two annular electrodes that extend about the circumference of the centrally located electrode.

In further embodiments, the electrodes of the circular electrode array are arranged electrically so as to form a bipolar electrode configuration, such that two of the three electrodes form an electrical circuit when in contact with the tissues so as to allow signals or current from the signal generating/sensing device to flow through the tissue and such that two of the three electrodes can sense a voltage or other electrical characteristic of the tissue when such signals or current is flowing through the tissue. In more specific embodiments, the first, inner annular electrode disposed between the centrally located circular electrode and the second, outer annular electrode is configured and arranged such that the signals or current generally flow proximal to the surface of the tissues. The centrally located circular electrode also is further configured and arranged such that the signals or current generally flow through tissues in a region that extends substantially beneath the surface of the tissues.

Other aspects and embodiments of the invention are discussed below.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein:

FIG. 2A is a block diagram illustrating a bioimpedance measuring apparatus or device according to the present invention with the cervix;

FIG. 2B is a block diagram illustrating an embodiment of the bioimpedance measuring device of FIG. 2A and also illustrating the current path through the apparatus to the cervical tissue;

DESCRIPTION OF THE PREFERRED EMBODIMENT

Figure 1A:
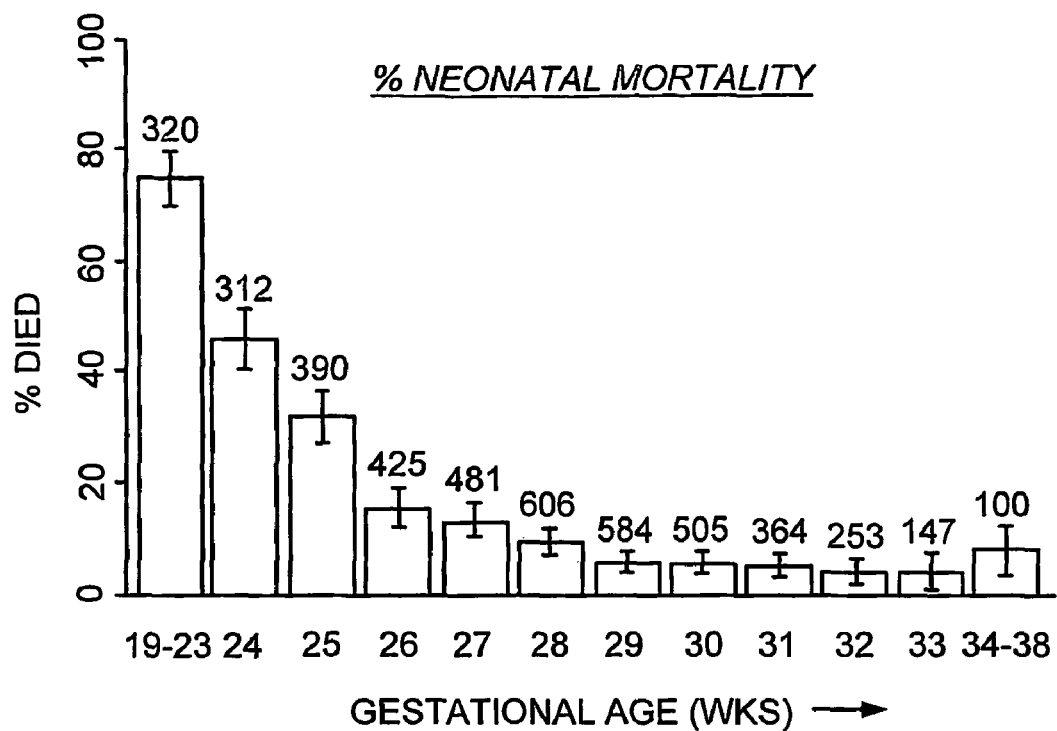
FIG. 1A is a graphical view showing percentage neonatial mortiality as a function of gestational age.
Figure 1B:
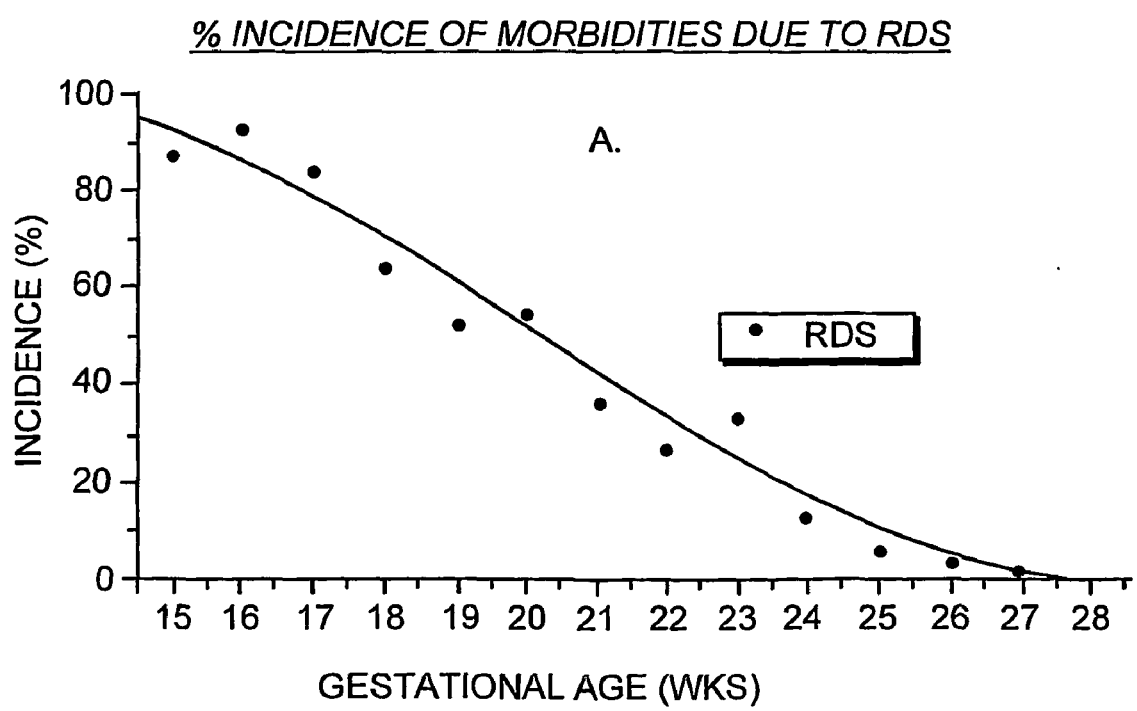
FIG. 1B is a graphical view showing the percent incidence of morbidities due to respiratory distress syndrome (RDS) as a function of gestational age.
Figure 3A:
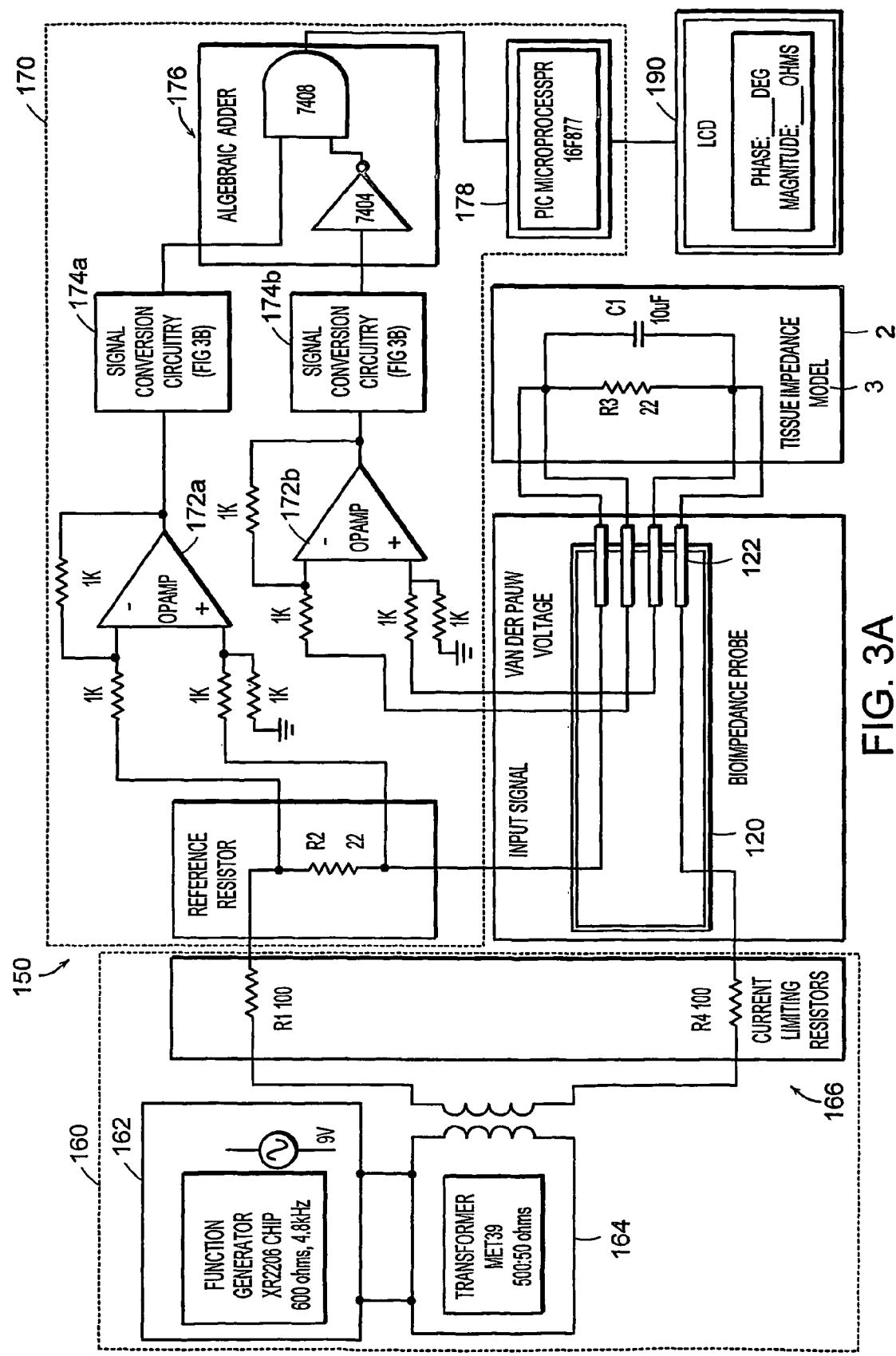
FIG. 3A is a complete schematic view including another embodiment of an illustrative bioimpedance measuring device, a tissue impedance model and a linear tetrapolar measuring probe according to the present invention.

Referring now to the various figures of the drawing wherein like reference characters refer to like parts, there is shown in FIG. 2A, a block diagram that illustrates a bioimpedance measuring apparatus 100 according to the present invention that includes a bioimpedance measuring device or bioimpedance measuring probe 120 and a signal generating and sensing device 150. The signal generating and sensing device 150 includes a signal generator 160 and a sensing device 170 each of which comprises circuitry to carry out the signal generation and sensing functions. The signal generating and sensing device 150 is operably and electrically coupled to the bioimpedance measuring probe 120 and this probe also is electrically coupled to the tissue of the cervix 2 via electrodes 122 (FIG. 3A). In this way and as shown more specifically in FIG. 3A, an electrical circuit or pathway is in effect established between the signal generating and sensing device 150 and the cervical tissues when the bioimpedance measuring probe 120 is in electrical contact with the tissues 3. As is known in the art, when such a pathway is established the signals (i.e., current/voltage) being generated by signal generating and sensing device 150, more specifically the signal generator 160 thereof, can flow through the cervical tissues 3.

As is shown in FIGS. 2B, 3A the signal generator 160 can include a function generator 162, a step down transformer 164 and an external source load 166. The magnitude and the frequency of the current being outputted is controlled so the outputted current passing through the sample can penetrate the cell membrane and effectively provide a measurement of the resistivity of the cervical tissue and the frequency is controlled so that the current disperses as is passes through the tissue thereby making it possible to measure an impedance (i.e., frequency is such that the current does not pass straight through the tissue without allowing sufficient dispersion of the current). In specific embodiments, the signal generator 160 is configured and arranged so the current passing through the tissue is limited so as not to be more than 0.5 mA, and the voltage being applied to be less than 3V. In further illustrative embodiments, the signal generator 160 is configured and arranged so that a sinusoidal current at 0.1 mA and 50 kHz is generated to pass through the cervical tissue 3 and the voltage being applied to the tissues is about 1.5V.

As is more particularly shown in FIG. 3A, the function generator 162 is a circuit formed around a single XR 2206 waveform generator IC. The circuit generates sine, square or triangle waves from 1 Hz to 1 MHz in four switched ranges. There are both high and low level outputs that may be adjusted with the level control. This XR 2206 IC contains an internal square wave oscillator, the frequency of which is controlled by timing capacitors and a potentiometer. The square wave is differentiated to produce a triangular wave, which in turn is shaped to produce a sine wave. Also included are two preset resistors that are provided to adjust the purity of the sine wave. The wave shape switch is a single pole 3 way rotary switch, the wiper arm selects the wave shape and is connected to a potentiometer which controls the amplitude of all waveforms.

At the high output, the maximum amplitude is about 3V peak to peak for the square wave and the maximum amplitude for the triangle and sine waves also is around 3V. In a preferred embodiment, the function generator is powered by a 9V DC source. Test have shown that for such a function generator, over the output range the distortion is less than 1%. A 9V battery or DC power source was chosen because it would not be necessary to maintain galvanic separation to ensure the safety of the patient, however it is within the scope of the present invention for the function generator to be powered using any of a number of power sources known to those skilled in that art and also for such power sources to provide appropriate galvanic separation for sources requires such actions.

The signal generator 160 include a step down transformer 164 for purposes of further stepping down the voltage being applied to the cervical tissues 3 for purposes of further ensuring safety for the mother and fetus. As more particularly shown in FIG. 3A, in an illustrative exemplary embodiment, the step down transformer is a MET31 (3:1) encapsulated transformer that is operably coupled to the output of the function generator 162. In more specific embodiments, the MET39 (3:1) encapsulated transformer is such that when the voltage inputted from the function generator 162 is 1.5V, the output voltage, which is the voltage being applied across the cervical tissue 3 is 0.5V.

In addition to providing a step down transformer, the signal generator includes an external load source 166, such as current limiting resistors, so as to thereby control the maximum current that can be generated and passed through the cervical tissues 3 thereby furthering safety of the patient and the medical personnel using the measuring apparatus 100. As the bioimpedance of the cervix 2 is not expected to exceed hundreds of Ohms, the use of a smaller current is appropriate. In illustrative embodiments the external load source 166 is an external load of about 3.3 kΩ, hence the output of the signal generator 160 consists of an applied voltage of 0.5V, thereby producing a maximum current of 0.14 mA at 50 kHz. As is shown in more detail in FIG. 3A, the output current of the signal generator 160 is passed through the probe 120, where it penetrates the cervical tissue 3. The resultant voltage decrease is thus measured with the sensing device 170.

Under certain conditions of frequency, current and voltage, mammalian tissues can exhibit an electrical characteristic such as an impedance or resistance much like any electrical circuit element (e.g., resistor). Thus, the bioimpedance measuring probe 120 also is electrically coupled to the tissues 3 of the cervix 2 so as to be capable of electrically coupling the electrical parameters (e.g., voltage) being sensed to the sensing device 170 of the signal generating and sensing device 170. The circuitry comprising the sensing device 170 determines or computes the electrical characteristic(s) being exhibited by the tissues based on the sensed information. In more specific embodiments, the sensing device also can provide an output (e.g., a visual display) of the observed or measured electrical characteristic(s). For example, the sensing device 170 can be any of a number of multimeter type of devices known to those skilled in the art that can be used to sense for example the resistance or impedance of ther tissues as well as phase angle.

In an illustrative embodiment, the sensing device is an Extech MM560 True-RMS Multimeter, which is a true RMS multimeter, that exhibits good resolution, enabling measurements up to 1 μV, 0.0001 Hz, 0.01 μA and 0.1°. The Extech model also is highly portable (less than 400 g), hence it can be integrated with the signal generating and sensing device 160. It also is battery powered, so an external source need not be provided to power the device. In addition, the Extech comes equipped with a software package that allows it to interface with a computer to enable easy data storage and analysis.

In another illustrative embodiment, and as is shown in FIG. 3A, two of the electrodes 122 the bioimpedance measuring probe 120 measures the resulting voltages in the cervical tissues 3 and the resulting voltage is amplified by a differential amplifier 172b, which also reduces the noise from the signals source, and the amplified signal is inputted to a signal conversion circuit 174a. Also, the signal output from the step down transformer 164 is appropriately processed and amplified by a differential amplifier 172a and inputted to a signal conversion circuit 174b.

Figure 3B:
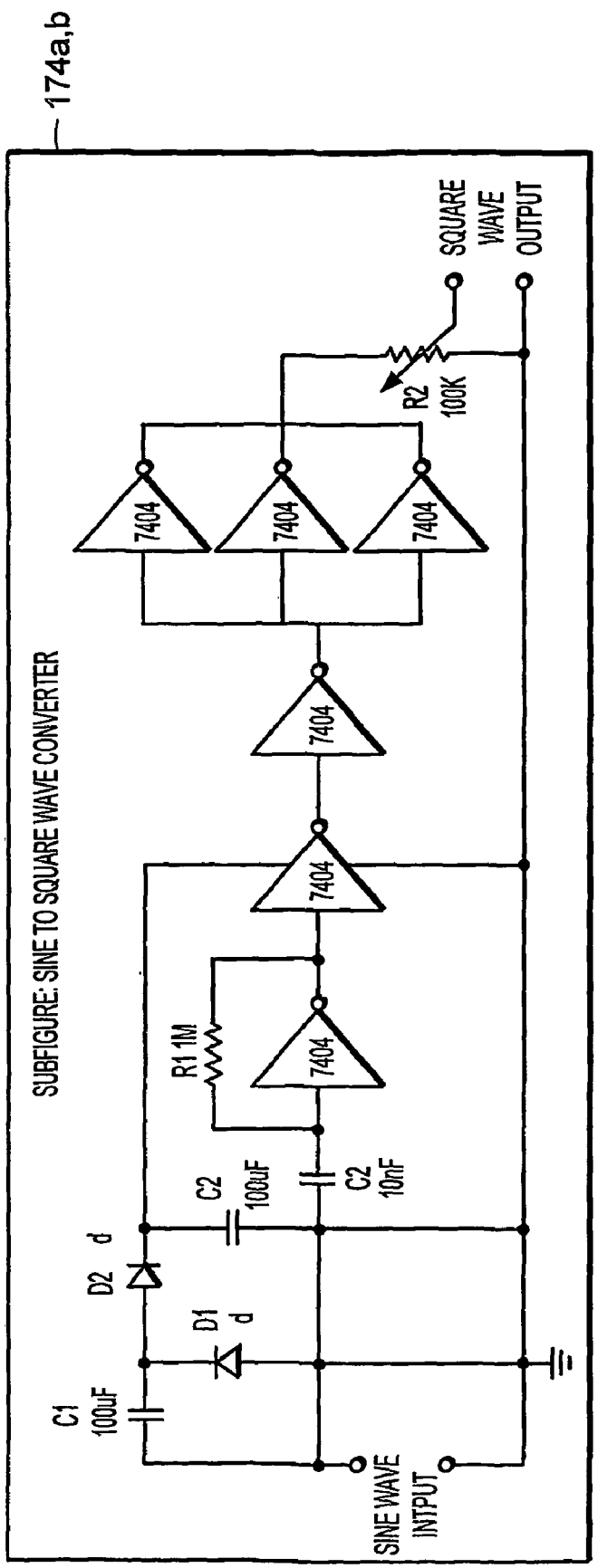
FIG. 3B is a schematic view of the signal conversion circuitry of FIG. 3A.

With reference also to FIG. 3B, the signal conversion circuits 174a,b are configured and arranged to convert the sinusoidal voltage signal being inputted into the respective signal conversion circuit to a square wave signal for example by a series of hex inverters. A sinusoidal wave is injected into the cervical tissues 3 because the properties of a square wave has an odd number of harmonics that would complicate the process of signal generation into the tissues 3. The voltage signals are converted to square wave signals because the zero-crossing points are comparatively much more evident to detect.

The two square signals outputted from respective signal conversion circuits 174a,b are then algebraically processed in an algebraic adder 176 comprised of a series of logic gates that is operably coupled to a Programmable Interrupt Controller (PIC 16F877) microprocessor chip 178. The PIC 178 measures the phase difference between the two signals. The phase measurement contains several parts. The input Ac current source passes through a reference resistor (wave A; pure resistance) and the actual cervical tissue (wave B: resistance+capacitance→Z=R+jX). The reference resistor value is chosen, for example, to be the average resistance value of non-pregnant women's cervical tissue. Wave B has a negative phase shift due to the capacitive effect of the cervical tissues 3. Because wave B also has issues with noise, a Schmidt trigger and low pass filter can be added to clean up the signal before phase analysis.

Subsequently, logic AND gates are used to algebraically subtract the two waves (waves A,B) and determine the difference between the two square waves (wave C), which provides information about the phase angle Using the sampling rate of the PIC, the timer of the PIC is used to measure and compute the width of wave C, which in turn, is the phase angle.

The measured values of the magnitude and phase are displayed, for example on an LCD 190 that is programmed or updated by the PIC chip 178. Since the refresh rate of the PIC 178 is rapid enough to seem continuous, a two line LCD display continuously shows the impedance measurements as being taken as in real time. In this way, the obstetrician-gynecologist, clinician or diagnostician using a look up chart can compare the measured impedance values to determine how the patient's reading(s) compare in terms of risk of labor induction. Preferably, in further embodiments, the LCD display is further controlled so as to automatically display additional information that relates to the risk of labor induction; in other words provide an indication that the reading is out of norm or providing an out of normal message instead of displaying the measured values.

Figure 3C:
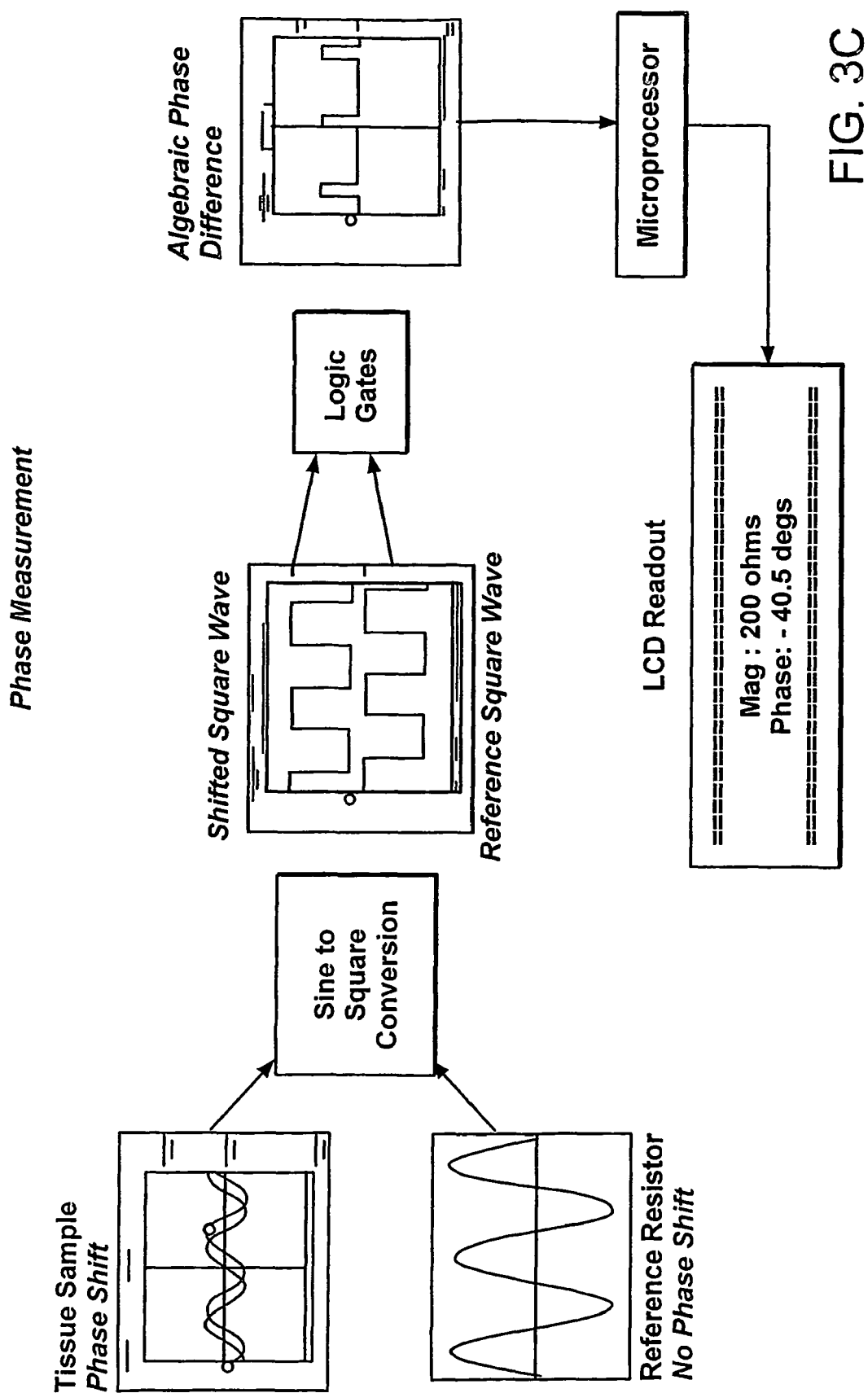
FIG. 3C illustrates the phase measurement process of the signal conversion circuitry of FIG. 3B.
Figure 4A:
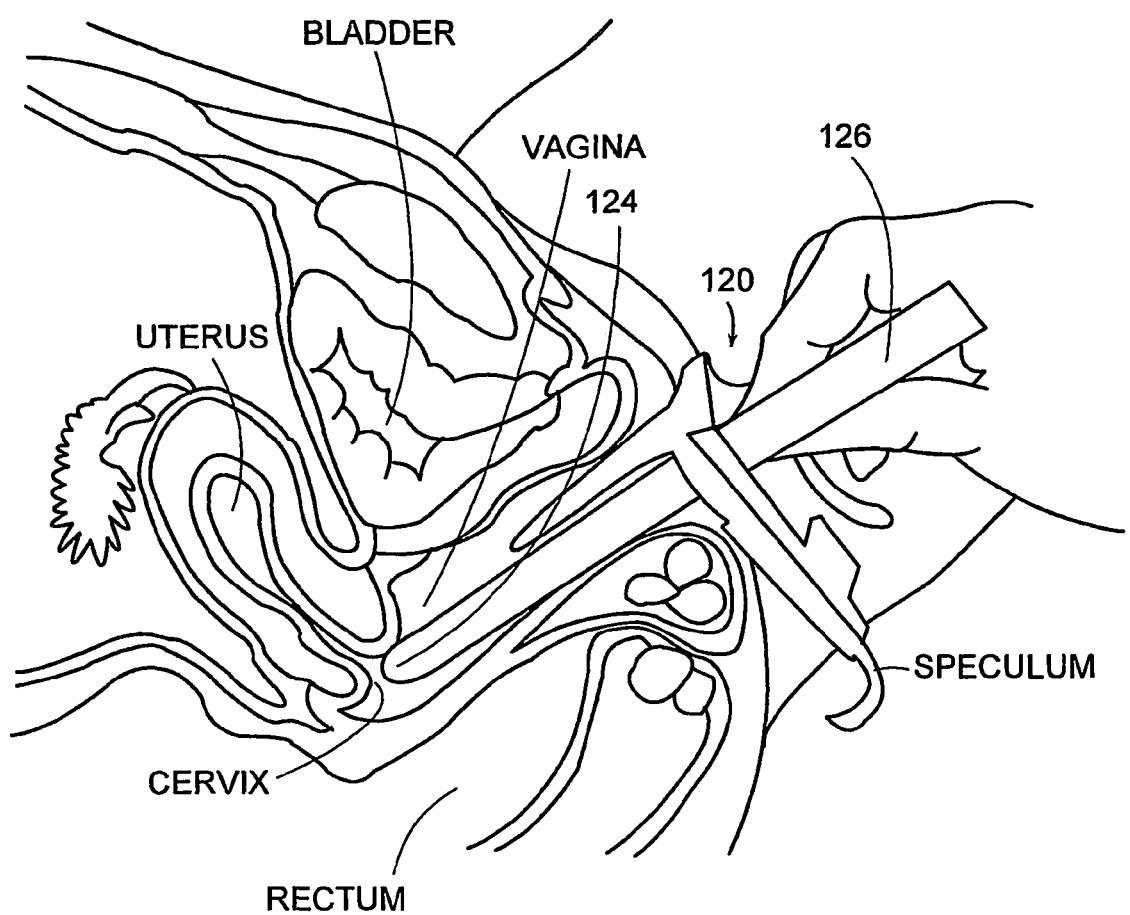
FIG. 4A is an illustrative showing insertion of a measuring probe according to any aspect or embodiment of the present into the vagina.
Figure 4B:
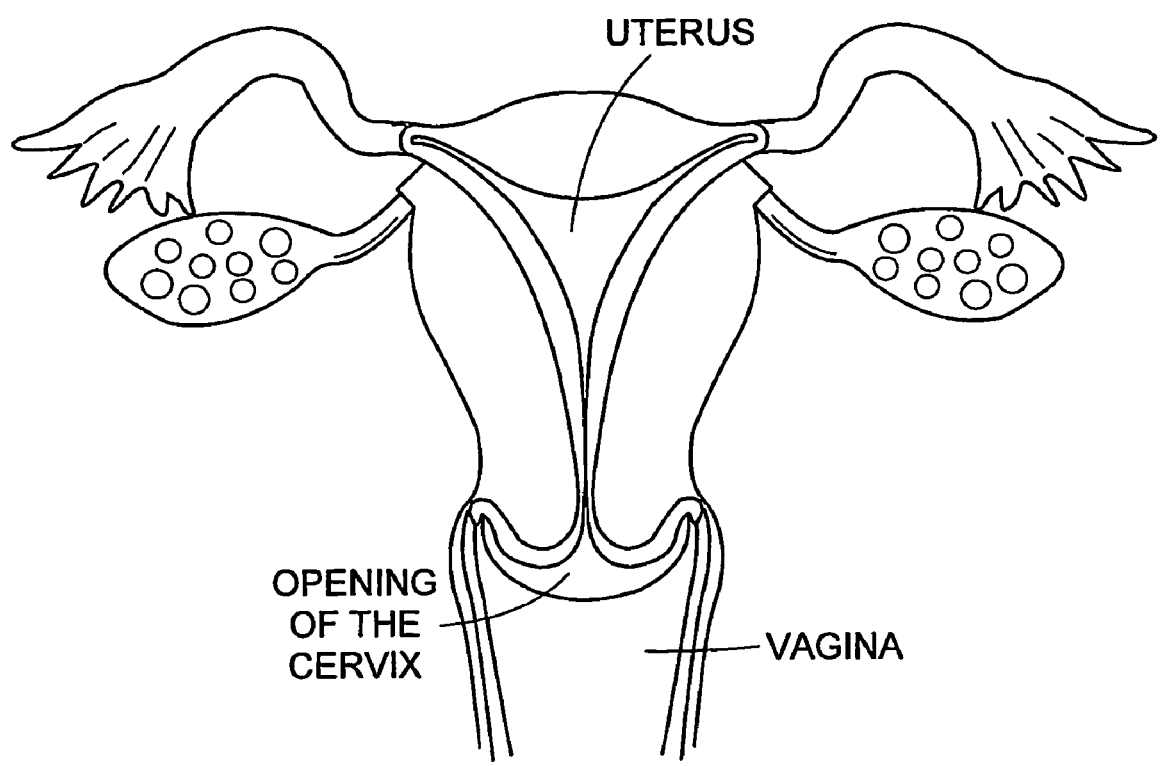
FIG. 4B is an anatomical view illustrating the anatomy of female reproductive organs.

The use of the bioimpedance measuring apparatus 100 can be best understood from the following discussion with reference to FIGS. 4A,B. Reference also should be made FIGS. 2-3 for further details of the bioimpedance measuring apparatus 100 not otherwise shown in FIG. 4A.

Prior to use, the bioimpedance measuring probe 120 is disconnected from the signal generating and sensing device 150 and the measuring probe is sterilized using any of a number of techniques known to those skilled in the art and compatible with the construction of the measuring probe. In an illustrative embodiment, the probe is sterilized in a standard autoclaving unit, according to the established protocols and methods for such use. To minimize the potential for damage, the autoclave's flash or quicker sterilization protocol may be used as opposed to the full cycle mode. As hereinafter provided, the materials comprising the measuring probe preferably are selected so as to be compatible with typical autoclave temperatures (e.g. 160° F.). After sterilization, the measuring probe is allowed to cool before it is re-coupled with the signal generating and sensing device 160. Another method of sterilization is to soak the probe in ethylene glycol solution after each use.

In alternative embodiments, the measuring probe 120 is sterilized and provided by the manufacturer in the sterilized condition in a kit or package. In such, a case, the sterilized measuring probe 120 would be removed from the protective packaging and coupled to the signal generating and sensing device 160.

The clinician/diagnostician/medical personnel (i.e., user) turns the signal generating and sensing device 150 on so as to be capable of outputting the desired current and voltage from the probe electrodes 122 to the tissues as well as being capable of sensing the desired electrical parameters (e.g., voltage) of the tissues and determining and outputting the desired parameter(s). The clinician/diagnostician then inserts the measuring probe 120 into an opening provided in the mammalian body, which in the illustrated embodiment is a natural bodily opening (i.e., the vagina). The measuring probe is inserted so that the tip member 124 of the probe is within the bodily opening and so a portion of the shaft member 126 remains outside so as to be handled or manipulated by the user. While the use of natural body opening is contemplated, it also is contemplated that the measuring probe could be inserted into an opening formed for example by surgical intervention.

The clinician/diagnostician or medical personnel further manipulates the measuring probe 120 such that the electrodes 122 are positioned proximal the tissues to be examined/evaluated and further manipulated such that all the electrodes contact these tissues. In more specific embodiments, the measuring probe 120 is manipulated so that the electrodes 122 are proximal to and in contact with tissues of the cervix. After inserting the measuring probe 120 and putting the probe electrodes 122 into contact with the cervical tissues 3, the measuring process begins and measured parameters would be displayed to the user.

As described herein, in further embodiments the bioimpedance measuring probe 120 is further configured and arranged so as to include a mechanism for manually controlling the application of the voltage and current to the probe electrodes 122. In this way, the probe electrodes 122 that would supply the current to the tissues are not energized as the device is being manipulated. This provides a further measure of safety to the patient, fetus and user. Thus, after inserting the probe and putting the probe electrodes 122 into contact with the cervical tissues 3, the clinician/diagnostician would actuate the control mechanism (e.g., switch) so the measuring process begins as described above.

After acquiring or measuring the bioimpedance parameter(s) and/or other related diagnostic information, the user can reposition the probe electrodes so they are oriented differently with respect to the cervical tissues. This would be accomplished by the user disengaging the probe electrodes 122 from the cervical tissue and manipulating the measuring probe 120 so that the electrodes are in a different orientation (e.g., rotate the measuring probe). After completing the measuring process, the user would withdraw the measuring probe from the opening in the body.

From the bioimpedance information obtained, the clinician/diagnostician can draw an inference about cervical tissue consistency, tensile strength and possible infiltration with neoplasm. Such information would assist and enhance important clinical management decision-making in a novel way, as "tissue-level" analysis will be made available in a non-invasive manner, as well as at an earlier time than when this information would otherwise have become evident or detectable clinically using conventional techniques.

Figure 5:
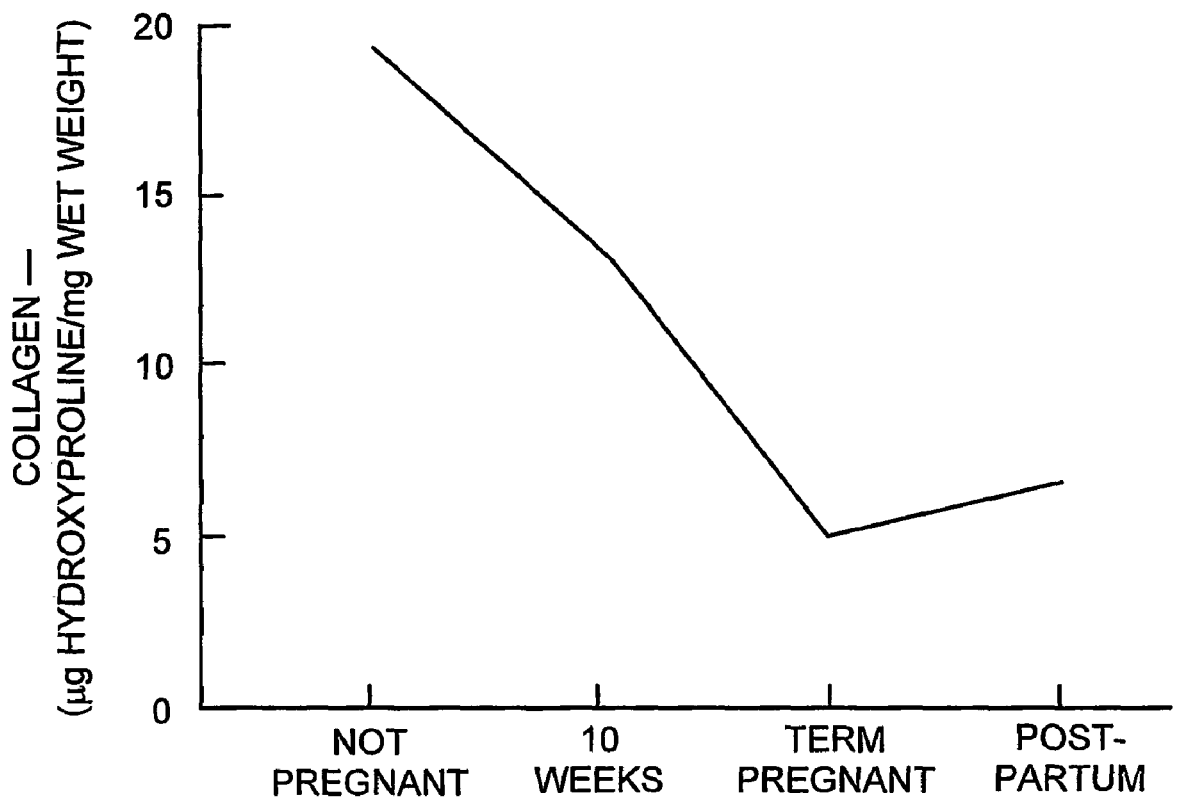
FIG. 5 is a graphical view illustrating the variation of collagen in the cervix versus gestation and post gestation.
Figure 6A:
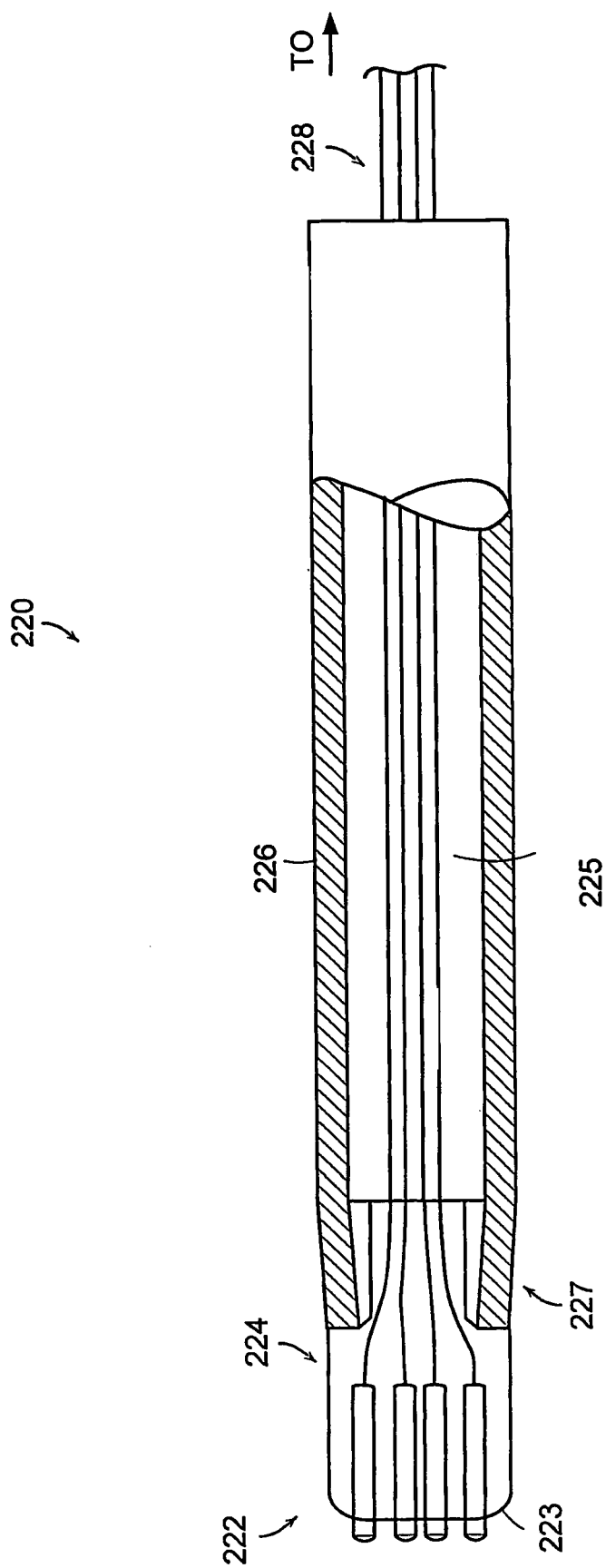
FIG. 6A is a partial cross-sectional side view illustrating a bioimedpance measuring probe according to one aspect of the present invention and configured with one of a plurality of tip embodiments.
Figure 6D:
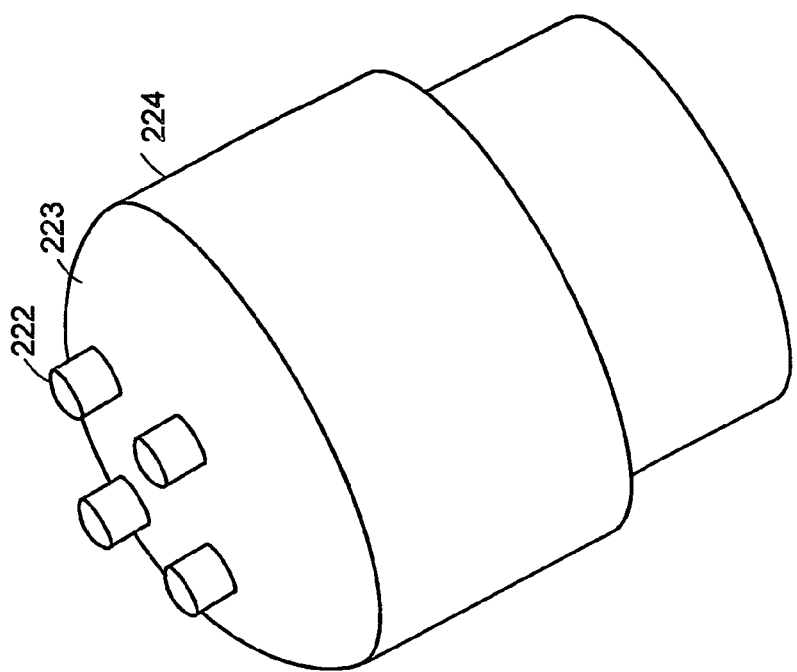
FIGS. 6B-D are top, side and perspective views respectively of a square tetrapolar probe tip embodiment.
Figure 6C:
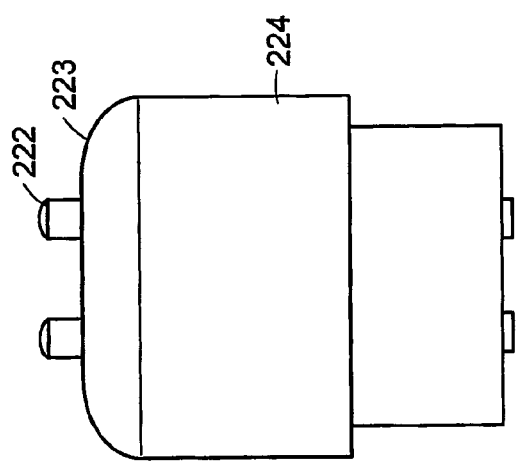
Figure 6B:
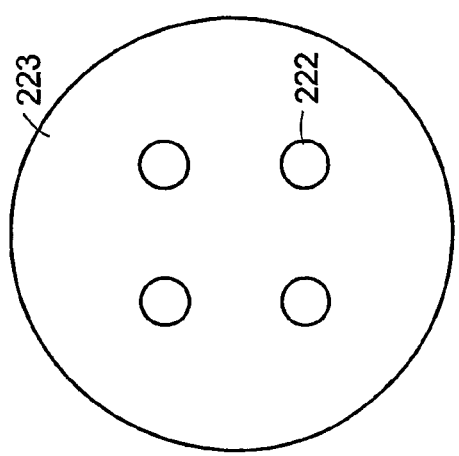

As indicated herein, there are many conditions that may result in pre-term delivery and that regardless of cause, the softening, dilation, and effacement of the cervix during pregnancy and labor do not occur as a result of uterine contractions alone, but are also a result of an active remodeling of the structure of the cervix. In the transition to labor, the tissue of the human pregnant cervix undergoes significant remodeling, such that its predominantly collagen matrix is replaced by glycosaminoglycans. This collagen matrix reduction can be seen from the graphical illustration provided in FIG. 5.

As a result of this "ripening," the cervix softens, thereby preparing for the thinning and dilation that will ultimately be required to allow the fetus to exit the womb. As the ratio of collagen to glycosaminoglycan decreases, the substance of the cervix becomes more hydrophilic. This is a feature or characteristic that should be measurable as changes in electrical conductivity of the tissue. Such changes in bioimpedance should be detectable at a tissue level well before it would be detectable clinically by digital palpation.

Since the methods of the present invention can provide earlier detection of the onset of labor as compared to conventional techniques, several treatments can be considered and implemented that can be very effective in delaying labor until an acceptable gestational age and level of fetal development occurs. As such, these treatments are expected to be more effective and safer to the pregnant women as detection is achieved or caught early in the gestation period. Also, because detection is likely to occur prior to rupture of the amniotic membrane, drugs that are otherwise not safe to use once the amniotic membrane has ruptured due to the increased medical risk of uterine and fetal infection, can be used for treatment.

Thus, in further embodiments, the clinician/diagnostician based on the results of the bioimpedance measurements can determine an appropriate treatment that can vary from something as simple as bed rest to drugs that can be administered in an effort to postpone labor or arrest its progression. Such drugs include, but are not limited to beta-adrenergic receptor agonists, magnesium sulfate, calcium channel blockers, cyclooxygenase inhibitors, salbumatol, lidocaine and nitric oxide/nitric oxide donors. Corticosteriods also are frequently employed as a specific treatment to the premature fetus to enhance organ maturation as well as improving fetal lung function by speeding development of the lungs and respiratory enzymes necessary for oxygen transfer. These also may decrease the risk of intraventricualar hemorrhage and injury to the gastrointestinal tract.

Referring now to FIGS. 6A-D, there is shown an embodiment of a bioimpedance-measuring probe 220 according to the present invention. The measuring probe 220 includes a top member 224, a shaft member 226, a plurality or more, more particularly four or more, more specifically four, electrodes 222 and interconnecting wires 228. The shaft member 226 includes an axially extending lumen or through aperture 225 in which pass the interconnecting wires 228. The shaft member 226 also is arranged so an end 227 thereof receives a portion of the top member 224 in the through aperture. In this way, the top member 224 is in mechanically engagement with the shaft member 226 so as the top member and shaft member form a unitary structure. In further embodiments, the top member 224 is in removable engagement with the shaft member 226 such that by application of a force, the top member can be removed from the shaft member for replacement or for other action.

The top member 224 is configured and arranged so that the electrodes are disposed in and extend from a top surface 223 of the top member and extend axially. Each electrode also is configured and arranged so as to have a length sufficient so one end of each electrode is located a predetermined distance from the top member top surface 223. Each of the electrodes 222 also are arranged so as to form or define a non-linear electrode array including a tetrahedral, rectilinear or circular array of electrodes. In a more specific and illustrative embodiment, the electrodes 222 are arranged in the top member 224 so as to form a square array that forms a square tetrapolar electrode array.

Figure 14:
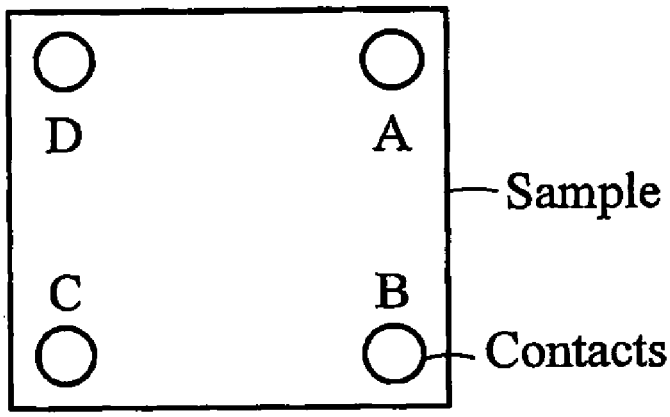
FIG. 14 illustrates the Van Der Pauw technique or method.

The interconnecting wires 228 interconnect each of the electrodes to a signal generating and sensing device 150 that is particularly configured and arranged for use with a square tetrapolar electrode array. A tetrapolar electrode array when used with the Van der Pauw technique of resistance measurement that allows one to obtain an averaged reading of the bioimpedance measurements. According to this technique, and with reference also to FIG. 14, the resistance reading is taken across 4 points on the sample area and the resistivity of the entire tissue is then computed by taking a geometrically corrected average of these readings. This technique is used in the present invention because the area of the tissue being samples is very small (~2 mm$^2$). Moreover, because the bioimpedance values within the cervical tissue may fluctuate, an averaged value affords greater consistency.

The Van der Pauw technique entails making a series of potential difference readings across four sample points defined on an arbitrary square sample or circular area. According to this technique a set of the probe electrodes 222 (i.e., any two of the four electrodes) are interconnected to the signal generator 160 and are supplied the current that is to flow through the cervical tissues. The other set of probe electrodes (i.e., the other two of the four electrodes) are coupled to the sensing device 167 so as to measure the potential difference. This setup is then rotated through all the possible probe electrode 222 combinations. Hence, two of the probe electrodes 222 are connected to the sensing device 170 tips for the potential difference measurement and two of the probe electrodes 222 are connected to the output from the signal generator 160 (after voltage and current have been stepped down by the transformer and external load respectively). Using the appropriate formulas for this technique, an averaged reading can be obtained.

In an exemplary illustrative embodiment, the electrodes 222 are secured in the top member 224. In an alternative embodiment, the electrodes 22 and top member 224 are configured and arranged using any of a number of techniques known to those in the art (e.g., spring loaded electrodes, sliding electrodes so that the electrodes are maintained in an essentially fixed relation laterally with respect to the top member top surface 223 and so that the electrodes can move axially or lengthwise so as to move inwardly or outwardly with respect to the top member top surface.

The top member 224 and shaft member 226 preferably have a cross-sectional shape and size that is appropriate for the intended use. In illustrative embodiments, when the top and shaft members 224,226 are secured to each other they generally form a cylindrical member sized so as to be capable of being inserted into the vagina during routine obstetrical or gynecological examinations as well as presenting a device that can be manipulated by the user. The length of the shaft member 226 is set so that the user can manipulate the bioimpedance measuring probe 220 outside of the body opening (e.g., vagina) as is illustrated in FIG. 3A.

Each of the top and shaft members 224, 226 are constructed of materials that are appropriate for the intended use and are biocompatible. The materials also are preferably suitable for the sterilization protocols (e.g., heating) that are used for sterilize the bioimpedance measuring probe 220 prior to its use in a medical procedure/insertion into a bodily opening. The materials for the shaft member 226 also are appropriate for the expected loads and forces that are imposed thereon while the shaft member is being manipulated and while the electrodes 222 are being maintained in engagement with the cervical tissues The electrodes are appropriately dimensioned for the intended us and are constructed from materials that are biocompatible and appropriate for the intended use. Such materials include gold, silver and copper and alloys thereof and in a specific embodiment the electrodes are made from a silver-copper alloy. It should be recognized that the foregoing is illustrative and that other materials, such as stainless steel, can be used if the electrical and material characteristics for such other materials are otherwise satisfactory for the intended use.

Referring now to FIGS. 7A-F there is shown various views of embodiments of a top member 324 that is configured and arranged so the electrodes 322 are arranged so as to form a one or more linear electrode arrays that extend widthwise or radially across the top surface 323 of the respective top member. Each of the one or more linear electrode arrays is comprised of a plurality or more of electrodes 322, more particularly four or more electrodes and in an exemplary illustrative embodiment, comprised of four electrodes. The electrodes 322 also are arranged so as to be spaced from each other so as to minimize field distribution problems and electrode irregularities. Such a linear electrode also yields a design having negligible electrode polarization. It is contemplated that the top members illustrated in FIGS. 7A-F would be used in combination with a shaft member such as the shaft member 226 shown in FIG. 6. As such, reference shall be made to the foregoing discussion for FIG. 6 for details of the shaft member.

Each of the linear electrode arrays comprises a linear tetrapolar probe electrode array in which two of the electrodes are electrically coupled to the signal generator 160 and the other two electrodes are electrically coupled to the sensing device 170. In an exemplary illustrative embodiment, the outer two electrodes of each linear array are electrically coupled to the signal generator 160 and the inner two electrodes of the array are electrically coupled to the sensing device 170 according to another embodiment of the present invention.

Figure 7C:
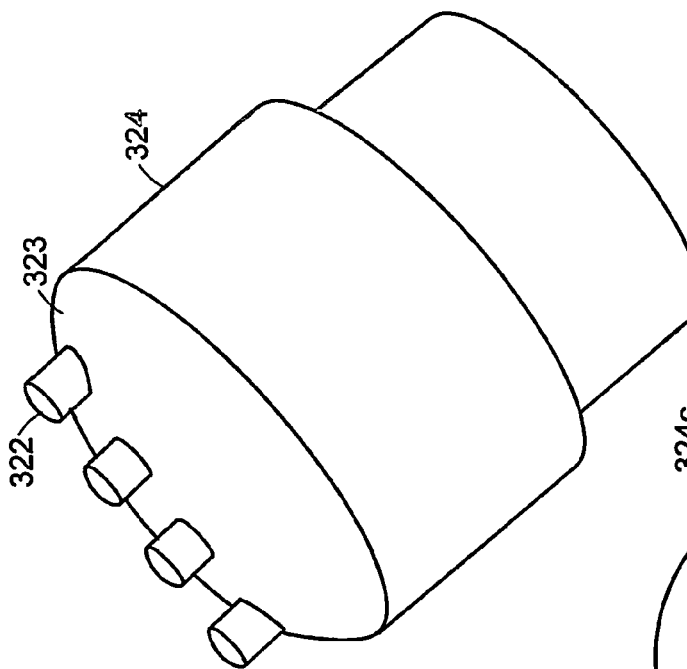
FIGS. 7A-C are top, side and perspective views respectively of a linear tetrapolar probe tip embodiment.
Figure 7B:
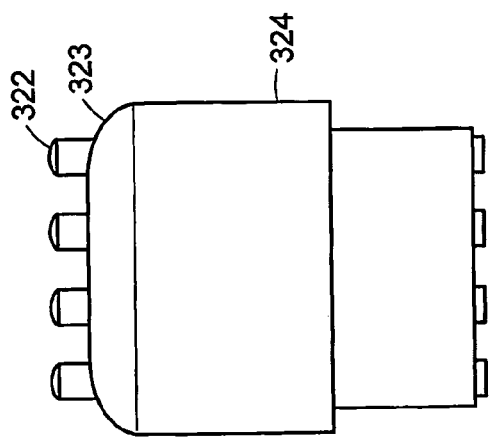
Figure 7A:
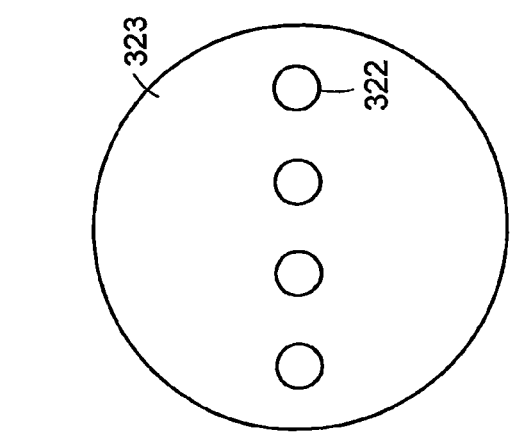

In the embodiment shown in FIGS. 7A-C, the electrodes 322 are spaced from the top member top surface 323 so that the exposed electrode end, the end that would contact the cervical tissues, is spaced the same from the top surface for all electrodes (i.e., the electrode ends for all electrodes lie in the same plane). Referring now to FIG. 7D, there is shown a top member 324a according ton another embodiment of the present invention. In this embodiment the lengths of the exposed portions of the electrodes are controlled so that the exposed electrode ends essentially mirror the opposing anatomical surface that they are to contact. In an illustrative embodiment, the lengths of exposed portions of the two inner electrodes extend further from the top surface 323 the exposed portions of the two outer electrodes.

Figure 7F:
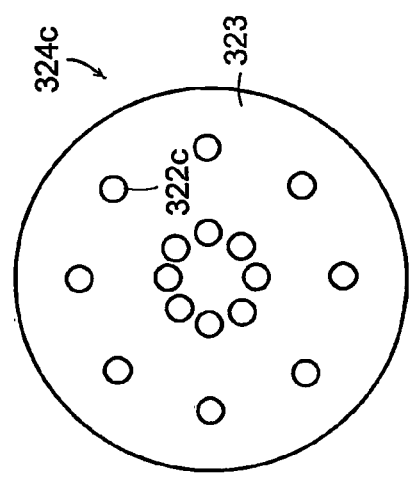
FIG. 7E-F are top views of further illustrative embodiments of a linear tetrapolar probe tip according to the present invention.
Figure 7E:
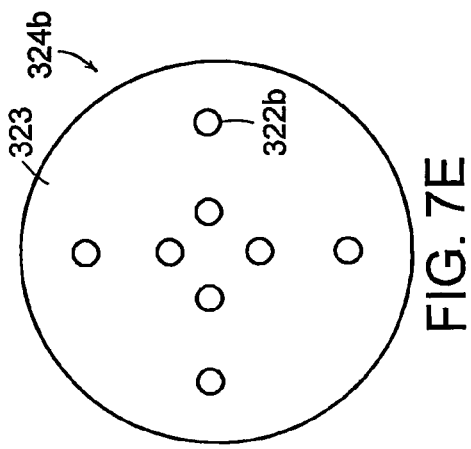
Figure 7D:
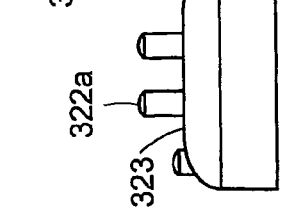
FIG. 7D is a side view of a linear tetrapolar probe tip according to another embodiment of the present invention.

Referring now to FIGS. 7E-F there are shown are top views of further illustrative embodiments of top members 324b,c that are configured with a plurality or more of linear electrode arrays. The top member 324b embodiment that is shown in FIG. 7E, is configured with two linear arrays that are arranged so that each are at an angle with respect to each other. In more particularly embodiments, the arrays are arranged such that a midpoint for each array is in common. In a more specific embodiment, the two linear electrode arrays are arranged so as to be orthogonal to each other. The top member 324c embodiment that is shown in FIG. 7F is configured so as to include a multiplicity or more of linear electrode arrays, more specifically eight linear electrode arrays, where the arrays are arranged so that each are at an angle with respect to adjacent linear array. It is within the scope of the present invention for the angle between adjacent arrays to be the same or different.

As indicated above, for the top member embodiments, shown in FIGS. 7A-D, two of the electrodes are coupled to the signal generating device 160 and the other two electrodes are coupled to the sensing device 170. In the embodiments shown in FIGS. 7E-F, it is within the scope of the present invention for the electrodes of each linear array to be selectively coupled to the signal generating device 160 and the sensing device so that the each linear array sequentially measures the bioimedance of the cervical tissues in the region bounded the linear array. In this way, the user can obtain a plurality or more of bioimedance measurements where the electrodes are in effect positioned at a different location from a prior arrangement and so the multiply acquired bioimedance values can be averaged so as to yield an average value.

Such an arrangement also avoids the need for the user to manipulate the shaft member 226 (FIG. 6A) so as to reposition the electrodes for each data acquisition. This thereby would speed up data acquisition as well as reducing stress and discomfort that could arise when a measuring probe was being manipulated so as to reposition the electrodes for another data acquisition.

Figure 8B:
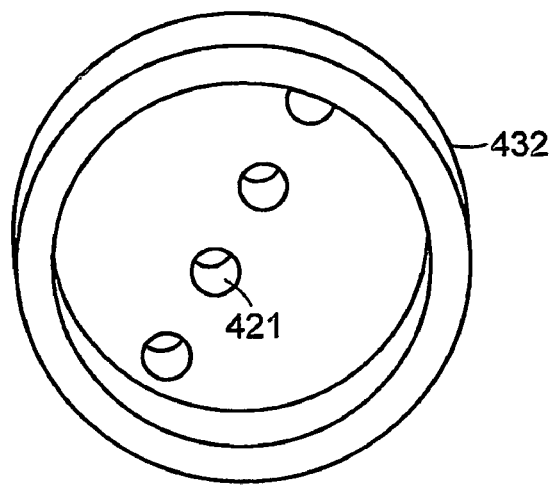
FIG. 8B is a perspective view of the bottom of the disposal tip member of FIG. 8A.
Figure 8A:
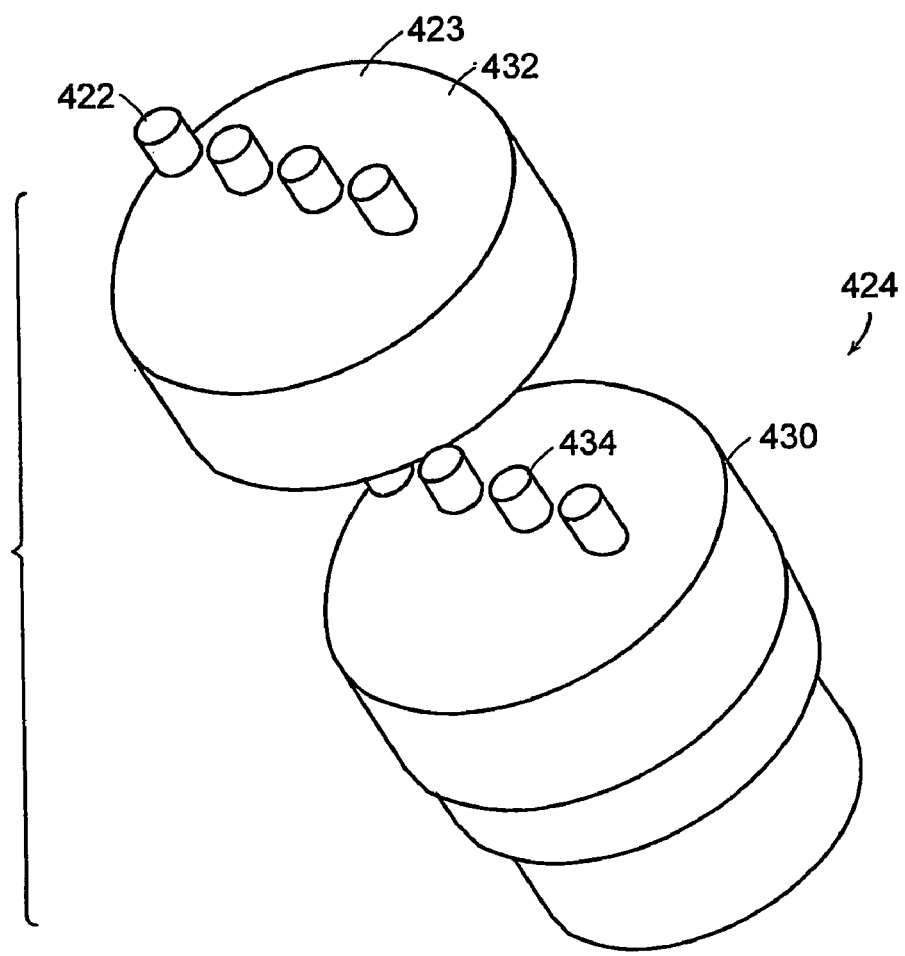
FIG. 8A is an exploded perspective views of another linear tetrapolar probe tip embodiment illustrating a disposal tip member.

Referring now to FIGS. 8A,B there is shown a top member 424 according to another aspect of the present invention that is configured and arranged so as to include a base portion 430 and a removable cover portion 432. It is contemplated that the top member illustrated in FIGS. 8A-B would be used in combination with a shaft member such as the shaft member 226 shown in FIG. 6. As such, reference shall be made to the foregoing discussion for FIG. 6 for details of the shaft member. Also while the embodiment illustrated in FIGS. 8A,B is that on a linear electrode array or a linear tetrapolar array, it is contemplated that any of the top member embodiments illustrated in any of FIGS. 6-7 can be configured so as to comprise a base portion and a removable cover portion.

The base portion 430 is secured to the shaft member 226 in the same manner as for any of the top members 224, 324 described in FIGS. 6-7 as such reference shall be made to the foregoing discussion. The base portion 430 also is configured and arranged so as to include a plurality of electrodes 434 extending outwardly from a top surface of the base portion. The base portion electrodes 434 also are arranged so as to mirror the arrangement for the electrodes 422 provided in the cover portion. In the illustrated embodiment, the base portion electrodes 434 are arranged to form a linear electrode array that mirrors the spacing and arrangement of the electrodes in the linear array formed in the cover portion 432.

In use, the cover portion is configured an arranged so as to include an open region 433 extending downwardly towards a bottom of the cover portion. The open region 433 and a mating surface of the base portion are preferably sized and configured so that cover portion removably, mechanically engage each other so the cover portion is retained on the base portion. In addition, the cover portion electrodes 422 are configured and arranged so as to form a pocket or axially extending aperture at a bottom edge thereof in which is received a corresponding portion one of the bottom portion electrodes 434 thereby forming a male-female type of electrical connection between these electrodes 422,434. It is contemplated that the cover portion electrodes 422 and the base portion electrodes 4334 may be adapted using any other connecting techniques known to those skilled in the art so as to form an electrical connection between corresponding electrodes when the cover portion 432 is removable secured to the base portion 430.

Figure 9C:
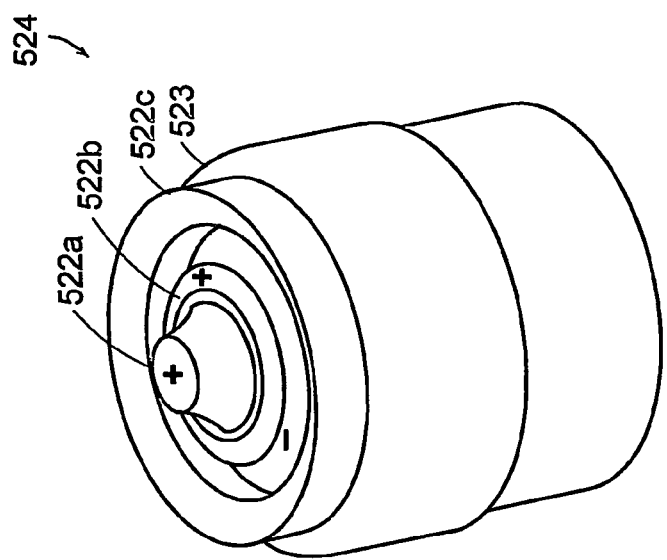
FIGS. 9A-C are top, side and perspective views respectively of a bipolar fit probe tip embodiment.
Figure 9B:
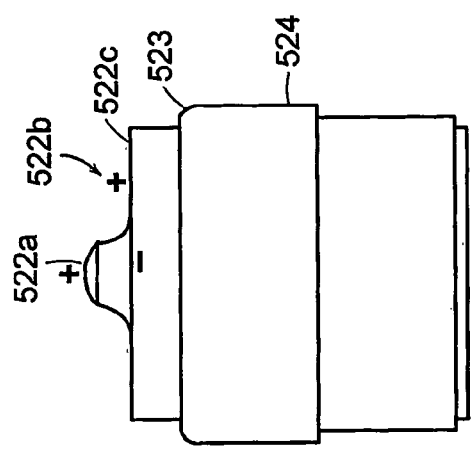
Figure 9A:
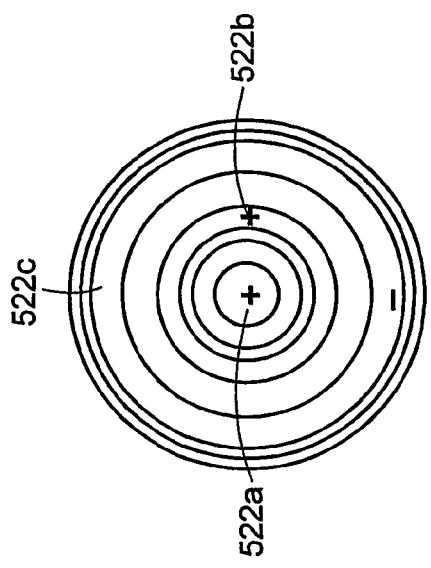
Figure 9D:
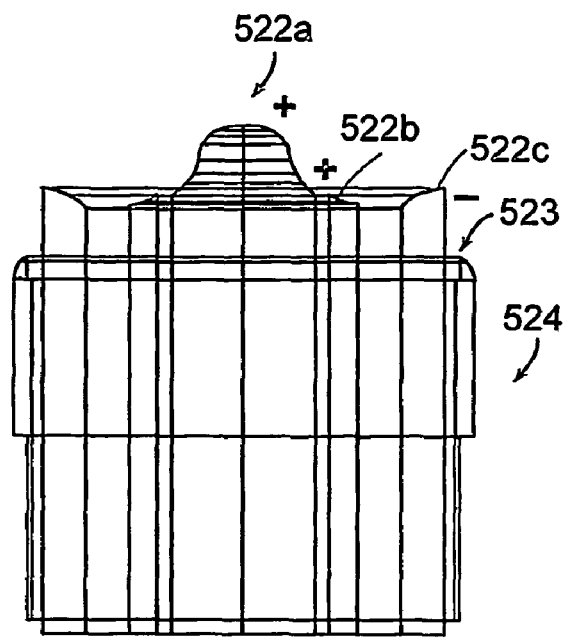
FIG. 9D is a schematic side view of the bipolar fit probe tip of FIG. 9B.
Figure 10:
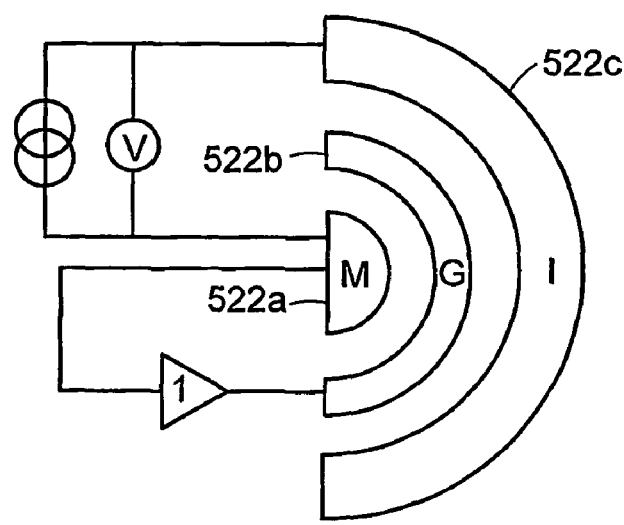
FIG. 10 is a schematic view illustrating the electrical coupling between the bipolar fit probe of FIGS. 9A-D with the signal generation and detection mechanism of the present invention.

Referring now to FIGS. 9-10 there is shown a top member 524 for a bipolar bioimpedance probe. It is contemplated that the top member illustrated in FIGS. 9A-D would be used in combination with a shaft member such as the shaft member 226 shown in FIG. 6. As such, reference shall be made to the foregoing discussion for FIG. 6 for details of the shaft member. Such a top member includes a central electrode 522a, an inner annular electrode 522b that is arranged so as to extend about the circumference of the central electrode and an outer annular electrode 522c that is arranged so as extend about the circumference of the inner annular electrode.

As is more clearly appears in FIGS. 9B-D, the ends of each of the central and annular electrodes 522a-c are each configured and arranged to mirror the contacting surfaces of the opposing cervical tissues. In addition, the central electrode 522a is configured and arranged so as the current being injected into the cervical tissues by the central electrode will reach a desired depth within the cervical tissues. Also, the inner annular electrode 522b is configured and arranged so as the current being injected into the cervical tissues by the central electrode will generally remain at the surface of the tissue. This further biases the current being injected from the central electrode 522a so it reaches deeper within the cervical tissues.

In use, and as illustrated in FIG. 10, the central electrode and the inner annular electrode are coupled to the signal generating device 160 so that the same voltage is being applied to the cervical tissues by these two electrodes and the outer annular electrode 522c forms or completes the electrical circuit. As also shown in FIG. 10, the sensing device is arranged so as to extend between two of the electrodes so as to measure the voltage in the tissue.

Reference shall be made to the foregoing discussion regarding FIGS. 6-7 as to the materials for the top member 524 and the electrodes, although it is contemplated that the electrodes can be made from other electrically conductive materials.

Figure 11:
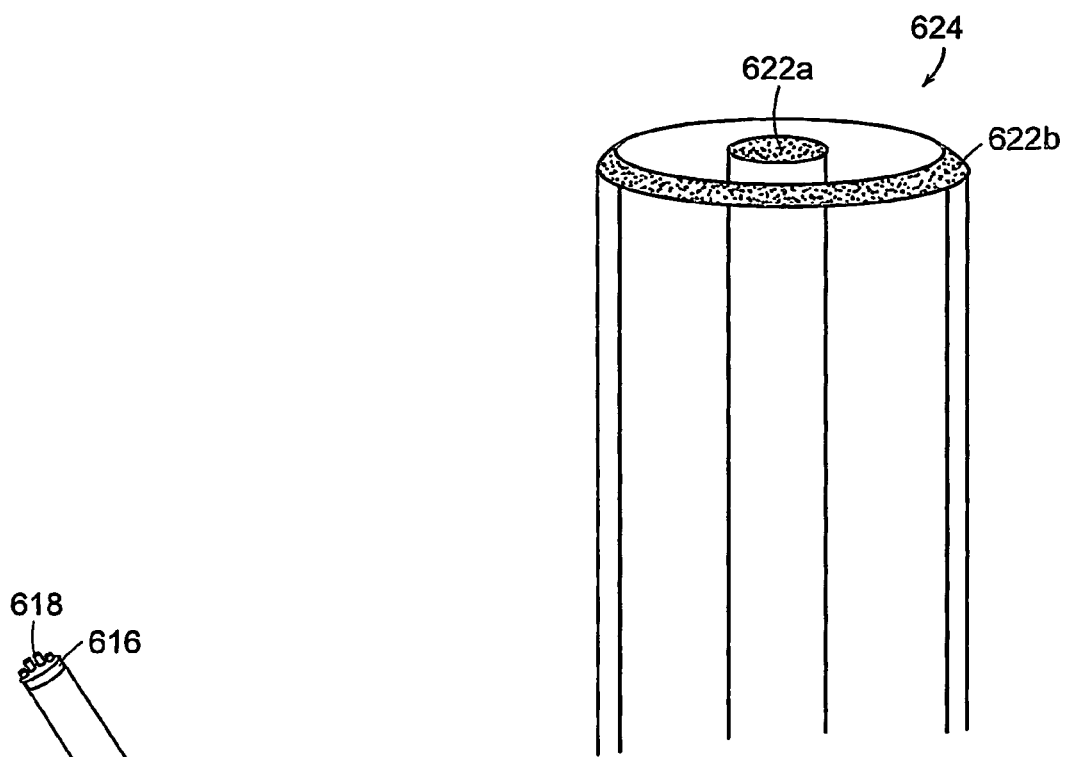
FIG. 11 is a perspective view of another bipolar probe tip according to the present invention.

Referring now to FIG. 11, there is shown an exploded view of a bioimpedance measuring apparatus 600 according to another aspect of the present invention. Such an apparatus includes a bioimpedance measuring probe 610, a spring 620 and a handle member 650. The bioimpedance measuring probe 610 comprises any of the measuring probes described herein but wherein the shaft member 612 would be configured so as to further include a stop 614 upon which one end of the spring 620 would rest.

The handle member 650 is configured an arranged so as to house the signal generating and sensing device 150 including the signal generator 160 and the sensing device 170 and an LCD display 190. The handle member 650 also is configured with an axially extending aperture having a base or end, and in which aperture is received the spring 620 and a portion of the shaft member 612. The other end of the spring 620 would rest upon the base or end of the handle aperture 652 when the measuring apparatus 600 is assembled.

In use, the user would manipulate the handle member 650 to insert the top member 616 into the bodily opening and thereafter manipulate the handle so as to cause the electrodes 618 to be positioned proximal to and in contact with the cervical tissues 3 (FIG. 4A). The spring 620 is preferably configured and arranged such that the electrodes are generally maintained in continuous contact with the cervical tissues and without a an appreciable variance in the force being applied to the tissues by the electrodes regardless of any force variations that may be introduced by a movement of the handle. In this way, because the force being exerted by the electrodes on the tissues should not significantly vary, the bioimpedance being measured should not appreciably fluctuate even when the force being applied to the handle varies. Also, it is preferable that the spring is configured so as to limit the maximum force that can be applied by the axial movement of the handle so as to be less than a desired value.

Figure 12:
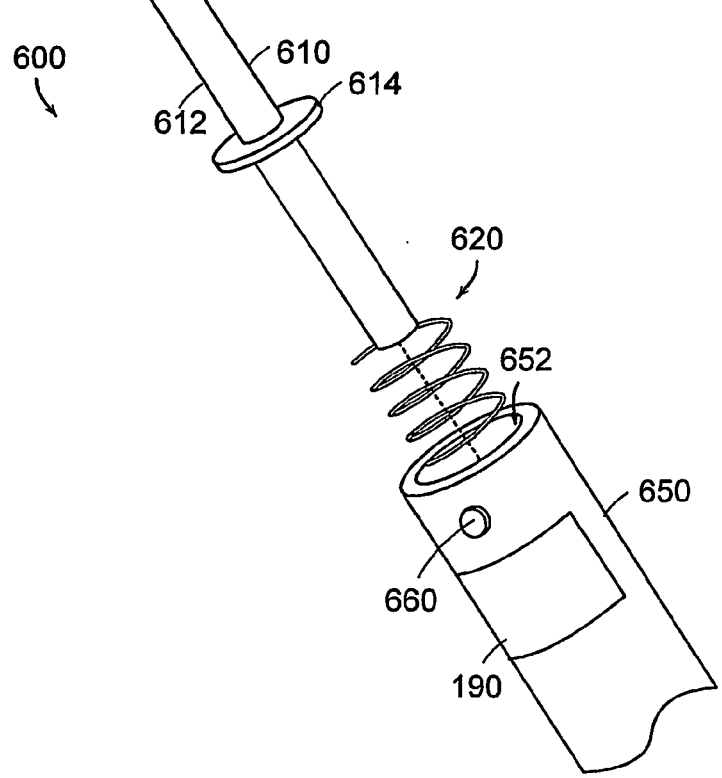
FIG. 12 is an exploded perspective view of a bioimpedance measuring apparatus or device according to another aspect of the present invention.

As also shown in FIG. 12, and as described herein, the handle member 650 is arranged so as to include a mechanism, switch or button 660 that is used to control the activation of the signal generator 160 and/or the electrical interconnection of the signal generator to the one or more electrodes that inject the current into the cervical tissues. In such an embodiment, the circuitry and button 660 would be arranged such that current does not flow, nor is a voltage applied across the electrodes except and when the button 660 is actuated.

Figure 13:
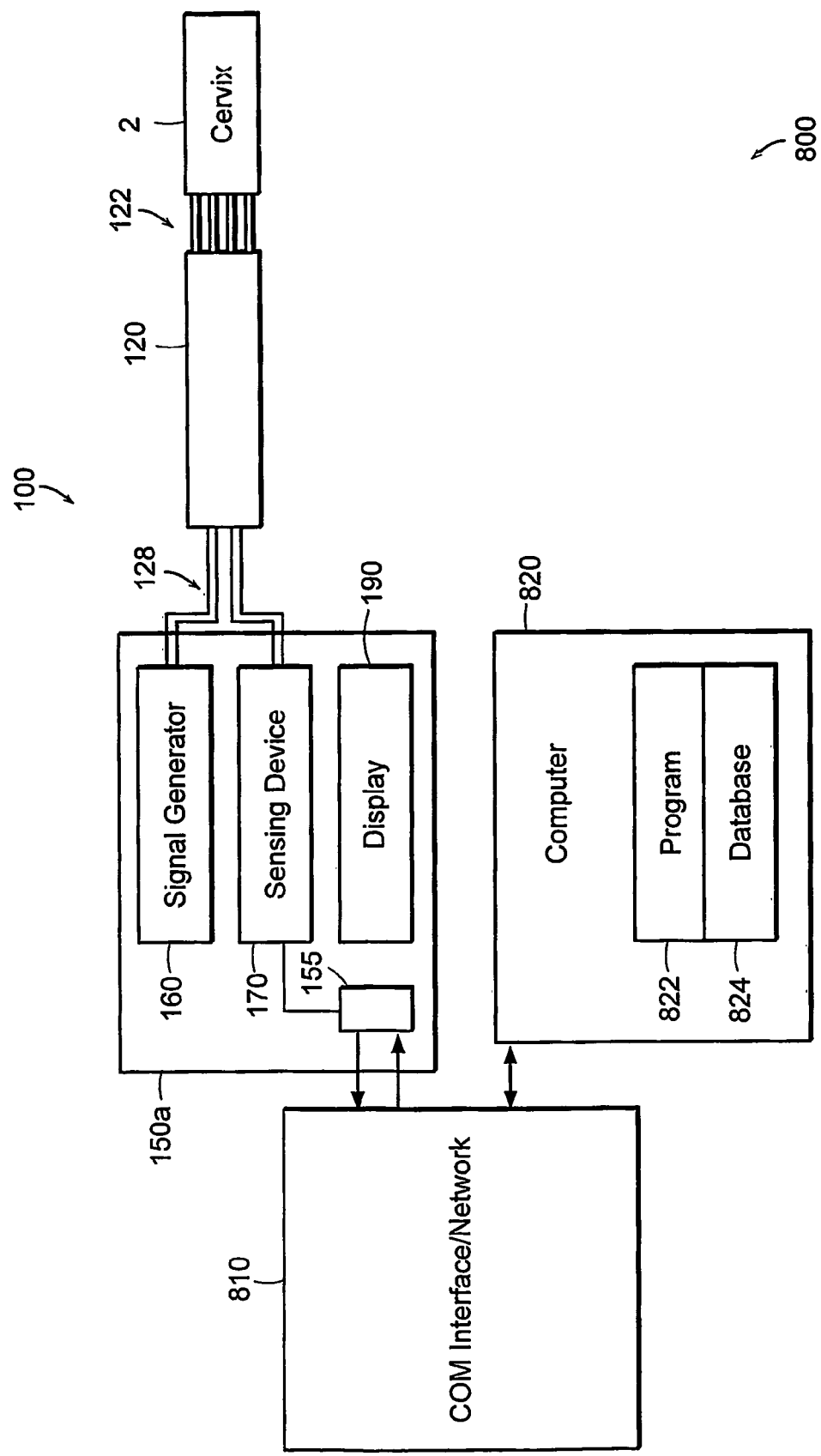
FIG. 13 is a block diagram view illustrating one bioimpedance measuring and analysis system according to the present invention.

Referring now to FIG. 13, there is shown a bioimpedance measuring system 800 according to the present invention for use in combination with any of the bioimpedance measuring apparatuses 100, 600 disclosed and taught herein as well as any of the bioimpedance measuring devices also disclosed and taught herein. For illustration purpose, the following discussion refers to the bioimpedance measuring apparatus 100 of FIG. 2A and a the bioimpedance measuring device 120 of FIG. 2A, 3A. As such reference shall be made to the discussion for these figures as to further details of the features and elements of these apparatus and device not otherwise described below.

The bioimpedance measuring system 800 also includes a communication interface 810 and a computer processing system 820. The computer processing system 810 is any of a number of systems known to those skilled in the art and generally includes a microprocessor and random access memory in which are executed applications programs and operating systems that are for processing data, performance of calculations and controlling of I/O operations for example as well as permanent storage devices or memory systems (i.e., systems that retain information after power to computer systems is turned off) such as those embodying magnetic hard disks and/or optical disks, which storage systems also can comprise an external array of such magnetic hard disks and optical disks (e.g., RAID configuration).

The communications interface 810 is any of a number of communications systems, devices or apparatuses known to those skilled in the art by which information can be selectively communicated from an external input device, such as a signal generating and sensing device 150 of the present invention to the computer processing system 820. Such communication interfaces 810 can embody any of a number of communications techniques known to those skilled in the art, including wireless communication techniques (e.g., RF and IR), wired communication techniques (e.g., electrical signals and optical signals), and an interface device (e.g., docking station) as well as systems that embody a combination of such communication techniques. In addition, it shall be understood that a communication interface 810 according to the present invention also shall include wide array and local area networks as well as embodying communication systems where communication is effected via the Internet.

It also shall be understood that the while communication with a single computer processing system 820 is shown, this shall not be construed as a limitation on the present invention as it is contemplated that such communications can be made with between the bioimpedance measuring apparatus and more that one computer system. For example, acquired bioimpedance measurement data could be transferred to a computer system that is for the specific user and to another computer systems that is tasked to acquire data for histological analysis purposes. Alternatively, the computer processing system 820 is connected via the communications interface 810 or via another communications system to the another computer system for transmission of the historical data to the another computer system.

The signal generating and sensing device 150a of the present invention further includes a communication interface device 155 that is configured and arranged so as to provide a mechanism for transferring the data acquired by the sensing device 170 to the communication system(s)s embodied in the communication interface 810 and to the computer processing system 820. In further embodiments, the communication interface device 155 also is configured and arranged so as to receive an output from the computer processing system 820 and to input this to the display so that this information contained in the processing system output can be displayed on the display 190. In this way, diagnostic and clinical information that is based on the measured information can be provided to the clinician or diagnostician without requiring them to specifically access the computer processing system for such information.

In one exemplary embodiment, the communication interface device 155 is any of a number of wireless communication devices or a device for use with any of a number or wired communication techniques (e.g., Ethernet). It is contemplated that such the signal generating an sensing device 150a and the communication interface device 155 also are configured and arranged so that such data communication of the measured bioimpedance data is processed and outputted to the computer processing system 820 essentially in real time. In other words, the data is processed and sent to the computer processing system 820*n* as it is being acquired.

In another embodiment, the bioimpedance measurement data is acquired and stored in the signal generating and sensing device 150*a* as it is being acquired. Following acquisition of all of the data, the user would operably couple the communication interface device 155 to the communication interface 810 (e.g., connect a network cable or USB cable to the communication interface device 155 and to the network communication system/computer processing system) so that the acquired data is sent to the computer processing system for processing (e.g. batch mode processing).

The communication interface device 155 also can comprise a device including the appropriate electrical connections for docking with a docking station when the communication interface 810 includes or comprises a docking station. Typically, a communications link would have already been established between the docking station and the computer processing system 820. Thus, following acquisition of all data, the user would operably couple the communication interface device 155 to the docking station so that the acquired data is sent to the computer processing system for processing (e.g., batch mode processing) via the docking station.

In particular embodiments, the computer processing system 810 further includes an applications program(s) 822 and a database 824 that is stored in the permanent storage system that are for use in combination with a bioimpedance measuring apparatus according to the present invention. In one exemplary embodiment, the applications program would include instructions and criteria for acquiring the data and storing it in a predetermined fashion in the database so it can be later retrieved by the clinician/diagnostician for analysis and evaluation. For example, the diagnostician/clinician can access all of the measurement data acquired over a period of time for a given patient (e.g., different visits by the patient) to determine if the measurement data is indicating that any trends or changes are occurring so that the clinician can determine if further action should be taken. In an obstetrical setting, this could be a determination that there is an indication of the onset of pre-term labor thereby allowing the obstetrician or gynecologist to determine if action should be taken to delay such delivery (e.g., diagnosis bed rest). In a non-obstetrical setting the clinician/diagnostician could use the information to determine if further tests should be undertaken to determine the cause for such changes. The information also could be used as further confirmation of the results of another type of test (e.g., pap smear) before proceeding with more invasive examination or diagnostic techniques (e.g., biopsy).

In yet further embodiments, it is contemplated that the database also include histological information that relates bioimpedance measurements to more specific clinical or diagnostic information as simple as for example that a given bioimpedance measurement is out of normal for the patient in question (e.g., age, pregnant or not pregnant, gestation time, etc). As such, the applications program would further include information and criteria to compare the histological data or information with the acquired measurement data and other pertinent input data and determine the histological clinical/diagnostic information that relates to the measurement data. The applications program also further include instructions and criteria for outputting such clinical/diagnostic information to the user for example displaying the information on the display 190.

Although a preferred embodiment of the invention has been described using specific terms, such description is for illustrative purposes only, and it is to be understood that changes and variations may be made without departing from the spirit or scope of the following claims.

INCORPORATION BY REFERENCE

All patents, published patent applications and other references disclosed herein are hereby expressly incorporated by reference in their entireties by reference.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A method for measuring the bioimpedance of cervical tissue, comprising the steps of:
    introducing a measuring probe within a bodily opening, the measuring probe including a plurality of electrodes arranged so that ends thereof are spaced a predetermined distance from an external end surface of the probe and so that the plurality of electrodes form a predetermined pattern that extends in a plane;
    positioning the measuring probe top surface with respect to the cervical tissues such that each of the electrodes is put into electrical contact with the cervical tissue;
    applying a voltage and current across certain of the plurality of electrodes in contact with the tissues so that the current flows through the tissues and is dispersed responsive to the impedance of the tissue;
    measuring the voltage drop associated with the tissue impedance using certain of the plurality of electrodes while said applying the voltage and current;
    computing an impedance and voltage phase angle based on the measured voltage;
    wherein the measuring probe includes three or more electrodes; and
    wherein said applying includes applying the voltage and current across three of the electrodes and wherein said measuring of the voltage drop is performed using two electrodes, where one of the electrodes for said measuring and said applying are in common.

2. The bioimpedance measuring method of claim 1, wherein the measuring probe being introduced includes one of three of four or more electrodes, eight or more electrodes or N×4 electrodes where N is an integer ≧2.

3. The bioimpedance measuring method of claim 2, wherein said applying includes applying the voltage and current across two of the electrodes and said measuring is performed using two electrodes.

4. The bioimpedance measuring method of claim 3, wherein:
    the probe being introduced includes four or more electrodes that are arranged so as to form a linear electrode array;
    said applying the voltage and current across two electrodes of the linear array, and
    said measuring includes measuring the voltage drop using the pairs of electrodes formed by the remaining two or more electrodes of the linear array.

5. The bioimpedance measuring method of claim 3, wherein:
the probe being introduced includes four electrodes that are arranged so as to form a linear electrode array;
said applying includes successively applying the voltage and current across two of the four electrodes forming the four electrode linear array, and
said measuring includes measuring the voltage drop using two other of the four electrodes forming the four electrode linear array.

6. The bioimpedance measuring method of claim 1, further including the step of removing the measuring probe from within the bodily opening after completing at least said measuring.

7. A method for measuring the bioimpedance of cervical tissue, comprising the steps of:
introducing a measuring probe within a bodily opening, the measuring probe including a plurality of electrodes arranged so that ends thereof are spaced from a top surface of the probe;
positioning the measuring probe top surface with respect to the cervical tissues such that each of the electrodes is put into electrical contact with the cervical tissue;
applying a voltage and current across certain of the plurality of electrodes in contact with the tissues so that the current flows through the tissues and is dispersed responsive to the impedance of the tissue;
measuring the voltage drop associated with the tissue impedance using certain of the plurality of electrodes while said applying the voltage and current;
computing an impedance and voltage phase angle based on the measured voltage;
wherein the probe being introduced includes four electrodes that are arranged so as to form a tetrahedral array;
wherein said applying includes successively applying the voltage and current across each of the pairs of electrodes of the four electrode array, and
wherein said measuring includes measuring the voltage drop using another of the pairs of electrodes of the four electrode array, the electrodes of the another pair being different from the electrodes used for said applying.

8. The bioimpedance measuring method of claim 7, wherein the tetrahedral array is in the form of a square.

9. A method for detecting the onset of labor, comprising the steps of:
introducing a measuring probe within a bodily opening, the measuring probe including a plurality or more of electrodes arranged so that ends thereof are spaced from a top surface of the probe;
positioning the measuring probe top surface with respect to the cervical tissues such that each of the electrodes is put into electrical contact with the cervical tissue;
applying a voltage and current across certain of the electrodes in contact with the tissues so that the current flows through the tissues and is dispersed responsive to the impedance of the tissue;
measuring the voltage drop associated with the tissue impedance while said applying the voltage and current;
computing an impedance and voltage phase angle based on the measured voltage; and
determining if the computed parameters are indicative of cervical tissue conditions associated with onset of labor.

10. The labor detecting method of claim 9, wherein the measuring probe being introduced includes one of three of more electrodes, four or more electrodes, eight or more electrodes or N×4 electrodes where N is an integer ≧2.

11. The labor detecting method of claim 10, wherein said applying includes applying the voltage and current across three of the electrodes and said measuring of the voltage drop is performed using two electrodes, where one of the electrodes for said measuring and said applying are in common.

12. The labor detecting method of claim 10, wherein said applying includes applying the voltage and current across two of the electrodes and said measuring is performed using two electrodes.

13. The labor detecting method of claim 12, wherein:
the probe being introduced includes four electrodes that area arranged so as to form a tetrahedral array;
said applying includes successively applying the voltage and current across each of the pairs of electrodes of the four electrode array, and
said measuring includes measuring the voltage drop using another of the pairs of electrodes of the four electrode array, the electrodes of the another pair being different from the electrodes used for said applying.

14. The labor detecting method of claim 13, wherein the tetrahedral array is in the form of a square.

15. The labor detecting method of claim 12, wherein:
the probe being introduced includes four or more electrodes that are arranged so as to form a liner electrode array;
said applying the voltage and current across two electrodes of the linear array, and
said measuring includes measuring the voltage drop using the pairs of electrodes formed by the remaining two or more electrodes of the linear array.

16. The labor detecting measuring method of claim 15, wherein:
the probe being introduced includes a plurality or more of linear arrays each array including four electrodes;
said applying includes successively applying the voltage and current across two of the four electrodes forming each of the plurality or more of linear arrays, and
said measuring includes measuring the voltage drop using two other of the four electrodes forming each of the plurality or more of linear arrays.

17. The labor detecting method of claim 15, wherein said applying includes applying the voltage and current across the outer two electrodes forming each linear array.

18. The labor detecting method of claim 9, further comprising the step of:
performing in a time sequence said steps of introducing, positioning, applying, measuring and computing so as to yield a plurality or more of computed time sequenced impedances and voltage phase angles; and
wherein said determining includes determining if the computed parameters in a time sequence are indicative of cervical tissue conditions associated with onset of labor.

19. A method for delaying onset of labor, comprising the steps of:
introducing a measuring probe within a bodily opening, the measuring probe including a plurality or more of electrodes arranged so that ends thereof are spaced from a top surface of the probe;
positioning the measuring probe top surface with respect to the cervical tissues such that each of the electrodes is put into electrical contact with the cervical tissue;
applying a voltage and current across certain of the electrodes in contact with the tissues so that the current flows through the tissues and is dispersed responsive to the impedance of the tissue;
measuring the voltage drop associated with the tissue impedance while said applying the voltage and current;

computing an impedance and voltage phase angle based on the measured voltage;

determining if the computed parameters are indicative of cervical tissue conditions associated with onset of labor; and performing a labor delaying technique based on said determining and gestation time.

20. The labor delaying method of claim 19, wherein the measuring probe being introduced includes one of three of more electrodes, four or more electrodes, eight or more electrodes or N×4 electrodes where N is an integer ≧2.

21. The labor delaying method of claim 20, wherein said applying includes applying the voltage and current across three of the electrodes and said measuring of the voltage drop is performed using two electrodes, where one of the electrodes for said measuring and said applying are in common.

22. The labor delaying method of claim 20, wherein said applying includes applying the voltage and current across two of the electrodes and said measuring is performed using two electrodes.

23. The labor delaying method of claim 22, wherein:
the probe being introduced includes four electrodes that are arranged so as to form a tetrahedral array;
said applying includes successively applying the voltage and current across each of the pairs of electrodes of the four electrode array, and
said measuring includes measuring the voltage drop using another of the pairs of electrodes of the four electrode array, the electrodes of the another pair being different from the electrodes used for said applying.

24. The labor delaying method of claim 23, wherein the tetrahedral array is in the form of a square.

25. The labor delaying method of claim 22, wherein:
the probe being introduced includes four or more electrodes that are arranged so as to form a linear electrode array;
said applying includes applying the voltage and current across two electrodes of the linear array, and
said measuring includes measuring the voltage drop using the pair of electrodes formed by the remaining two or more electrodes of the linear array.

26. The labor delaying method of claim 25, wherein:
the probe being introduced includes a plurality or more of linear arrays each linear array including four electrodes;
said applying includes successively applying the voltage and current across two of the four electrodes of each of the plurality or more of linear arrays, and
said measuring includes measuring the voltage drop using two other of the four electrodes of each of the plurality or more of linear arrays.

27. The labor delaying method of claim 25, wherein said applying includes applying the voltage and current across the outer two electrodes of the linear array.

28. The labor delaying method of claim 19, further comprising the step of:
performing in a time sequence said steps of introducing, positioning, applying, measuring and computing so as to yield a plurality or more of computed time sequenced impedances and voltage phase angles; and
wherein said determining includes determining if the computed parameters in a time sequence are indicative of cervical tissue conditions associated with onset of labor.

29. The labor delaying method of claim 19, wherein said performing a labor delaying technique based on said determining and gestation time further includes:
instructing a patient to do at least one of bed rest or take drugs, the drugs being selected from the group consisting of beta-adrenergic receptor agonists, magnesium sulfate, calcium channel blockers, cyclooxygenase inhibitors, salbumatol, lidocaine and nitric oxide/nitric oxide donors.

30. The labor delaying method of claim 19, further comprising the step of:
administering corticosteriods to a patient in addition to said step of performing a labor delaying technique.

31. A bioimpedance measuring apparatus comprising:
a measuring probe being configured and arranged for removable insertion into a bodily opening, the measuring probe including a plurality of electrodes arranged so that ends thereof are spaced a predetermined distance from an external end surface of the probe and so that the plurality of electrodes form a predetermined pattern that extends in a plane;
a signal generator being configured and arranged so as to generate an application voltage and current;
a sensing device for sensing and measuring an electrical characteristic associated with tissue impedance;
wherein the signal generator is operably coupled to certain of the plurality of electrodes so that when these certain electrodes are in contact with the tissues the applied current flows through a region of the tissues and is dispersed responsive to the impedance of the tissue;
wherein the sensing device is operably coupled to certain of the plurality of electrodes so as to sense and measuring a voltage drop associated with the tissue impedance while the voltage and current is being applied to the region of the tissues;
a computing device being configured and arranged so as to compute an impedance and voltage phase angle using the measured voltage drop;
wherein the measuring probe includes at least three electrodes; and
wherein the signal generator is operably coupled to three electrodes and wherein said sensing device is operably coupled operably coupled to two of the three electrodes so as to sense and measure a voltage drop associated with tissue impedance.

32. The bioimpedance measuring apparatus of claim 31, wherein the measuring probe further comprises one of three or more electrodes, four or more electrodes, eight or more electrodes or N×4 electrodes where N is an integer ≧2.

33. The bioimpedance measuring apparatus of claim 31, wherein the three electrodes are configured and arranged so that they comprise in this order:
an inner circular electrode;
a first annular electrode disposed about the inner electrode; and
a second annular electrode disposed about the first annular electrode.

34. The bioimpedance device of claim 33, wherein the signal generator is operably coupled to each of the inner electrode, the first annular electrode and the second annular electrode.

35. The bioimpedance measuring apparatus of claim 34, wherein the inner electrode and the first annular electrode are each configured and arranged so that the current being applied via the inner electrode reaches a desired depth in the tissue and so that the current being applied via the first annular electrode passes proximal the surface of the tissue.

36. The bioimpedance measuring apparatus of claim 31, wherein:
the measuring probe further includes four electrodes arranged so as to form a linear electrode array, the signal generator is operably coupled to two electrodes of the four electrodes of the linear array so that the applied current flows through these electrodes and through a region of the tissues and is dispersed in the tissues responsive to the impedance of the tissue; and the sensing device is operably coupled to the other two electrodes of the array.

37. The bioimpedance measuring apparatus of claim 36, wherein:

the signal generator is operably coupled to the two outer electrodes of the linear array; and the sensing device is operably coupled to the two inner electrodes of the linear array.

38. A bioimpedance measuring apparatus comprising:

a measuring probe being configured and arranged for insertion into a bodily opening, the measuring probe including a plurality of electrodes arranged so that ends thereof are spaced from a top surface of the probe;

a signal generator being configured and arranged so as to generate an application voltage and current;

a sensing device for sensing and measuring an electrical characteristic associated with tissue impedance;

wherein the signal generator is operably coupled to certain of the plurality of electrodes so that when these certain electrodes are in contact with the tissues the applied current flows through a region of the tissues and is dispersed responsive to the impedance of the tissue;

wherein the sensing device is operably coupled to certain of the plurality of electrodes so as to sense and measuring a voltage drop associated with the tissue impedance while the voltage and current is being applied to the region of the tissues;

a computing device being configured and arranged so as to compute an impedance and voltage phase angle using the measured voltage drop;

wherein the measuring probe includes four electrodes arranged so as to form a tetrahedral array, wherein the signal generator is configured an arranged so as to be sequential and operably coupled to two electrodes of each of the four pairs of electrodes of the array so that the applied current flows successively through each of the four pairs of electrodes and the tissues and is dispersed responsive to impedance of the tissue;

wherein the sensing device is sequential and operably coupled to the two electrodes of the array not being operably coupled to the signal generator; and wherein the computing device computes an impedance and voltage phase angle for each of the four pairs of electrodes and an average value therefrom.

39. A bioimpedance measuring apparatus comprising:

a measuring probe being configured and arranged for insertion into a bodily opening, the measuring probe including a plurality of electrodes arranged so that ends thereof are spaced from a top surface of the probe;

a signal generator being configured and arranged so as to generate an application voltage and current;

a sensing device for sensing and measuring an electrical characteristic associated with tissue impedance;

wherein the signal generator is operably coupled to certain of the plurality of electrodes so that when these certain electrodes are in contact with the tissues the applied current flows through a region of the tissues and is dispersed responsive to the impedance of the tissue;

wherein the sensing device is operably coupled to certain of the plurality of electrodes so as to sense and measuring a voltage drop associated with the tissue impedance while the voltage and current is being applied to the region of the tissues;

a computing device being configured and arranged so as to compute an impedance and voltage phase angle using the measured voltage drop;

wherein the measuring probe includes N linear arrays, where $N \geq 2$, where each linear array includes four electrodes, and where the N linear arrays are arranged so as to be at an angle with respect to an adjacent array;

wherein the signal generator is configured and arranged so as to be sequentially and operably coupled to two electrodes of each array so that the applied current flows through these electrodes and through the region of the tissues and is dispersed in the tissues responsive to the impedance of the tissue;

wherein the sensing device is configured and arranged so as to be sequentially and operably coupled to the other two electrodes of said each array; and wherein the computing device computes an impedance and voltage phase angle for each of the linear arrays.

40. The bioimpedance measuring apparatus of claim 39, wherein each of the N linear arrays has a midpoint and wherein the midpoint for each of the N linear arrays is in common.

41. The bioimpedance measuring apparatus of claim 39, wherein the computing device computes an average value from the computed impedance and voltage phase angle for each of the linear arrays.

42. The bioimpedance measuring apparatus of claim 39, wherein $N=2$ and wherein the two linear arrays are arranged so as to be essentially orthogonal to each other.

43. The bioimpedance measuring apparatus of claim 39, wherein:

the signal generator is configured and arranged so that it is sequentially and operably coupled to the two outer electrodes of each linear array; and the sensing device is configured and arranged so that it is sequentially and operably coupled to the two inner electrodes of each linear array.

44. A bioimpedance measuring device for measuring a bioimpedance of tissue comprising;

a probe including a tip member and a shaft, the tip member being coupled to the shaft;

three electrodes extending outwardly a predetermined distance from a surface of tip member;

wherein the shaft has a length set so that a user can manipulate the probe external to an opening in a mammalian body and so that the electrodes can be placed into contact with the tissue; and wherein the three electrodes are configured and arranged so that they comprise in this order:

an inner circular electrode;

a first annular electrode disposed about the inner electrode; and a second annular electrode disposed about the first annular electrode.

45. The bioimpedance measuring device of claim 44, wherein the inner electrode and the first annular electrode are each configured and arranged so that when current is applied via the inner electrode the applied current reaches a desired depth in the tissue and so that when current is concurrently applied via the first annular electrode the applied current passes proximal the surface of the tissue.

46. A bioimpedance measuring device for measuring a bioimpedance of tissue, comprising:

a probe;

N linear arrays of electrodes, where N≧2, where each linear array includes four electrodes, and where the N linear arrays are arranged so as to be at an angle with respect to an adjacent array;

wherein the electrodes of each linear electrode array extend outwardly a predetermined distance from a surface of the probe; and wherein one pair of electrodes being for applying a current to the tissue and the other pair of electrodes being for measuring a voltage drop associated with impedance of the tissue.

47. A system for detecting the onset of labor; comprising:
a bioimpedance measuring apparatus;
a computer processing system operably coupled to the bioimpedance measuring apparatus: and
wherein the bioimpedance measuring apparatus includes:
a measuring probe being configured and arranged for removable insertion into a bodily opening, the measuring probe including a plurality of electrodes arranged so that ends thereof are spaced a predetermined distance from an external end surface of the probe and so that the plurality of electrodes form a predetermined pattern that extends in a plane,
a signal generator being configured and arranged so as to generate an application voltage and current,
a sensing device for sensing and measuring an electrical characteristic associated with tissue impedance,
wherein the signal generator is operably coupled to certain of the plurality of electrodes so that when these certain electrodes are in contact with the tissues the applied current flows through a region of the tissues and is dispersed responsive to the impedance of the tissue,
wherein the sensing device is operably coupled to certain of the plurality of electrodes so as to sense and measuring a voltage drop associated with the tissue impedance while the voltage and current is being applied to the region of the tissues,
wherein the measuring probe includes at least three electrodes,
wherein the signal generator is operably coupled to three electrodes and wherein said sensing device is operably coupled operably coupled to two of the three electrodes so as to sense and measure a voltage drop associated with tissue impedance, and
wherein the computer processing system is configured and arranged so as to compute an impedance and voltage phase angle using the measured voltage drop.

48. A system for detecting the onset of labor; comprising:
a bioimpedance measuring apparatus;
a computer processing system operably coupled to the bioimpedance measuring apparatus: and
wherein the bioimpedance measuring apparatus includes:
a measuring probe being configured and arranged for insertion into a bodily opening, the measuring probe including a plurality or more of electrodes arranged so that ends thereof are spaced from a top surface of the probe,
a signal generator being configured and arranged so as to generate an application voltage and current,
a sensing device for sensing and measuring an electrical characteristic associated with tissue impedance,
wherein the signal generator is operably coupled to certain of the plurality or more electrodes so that when these certain electrodes are in contact with the tissues the applied current flows through a region of the tissues and is dispersed responsive to the impedance of the tissue,
wherein the sensing device is operably coupled to certain of the plurality or more of electrodes so as to sense and measuring a voltage drop associated with the tissue impedance while the voltage and current is being applied to the region of the tissues, and
a computing device being configured and arranged so as to compute an impedance and voltage phase angle using the measured voltage drop and to output the computed impedance and voltage phase angle to said computer system, and
wherein said computer processing system includes:
a database for storing in a time sequence the computed impedance and phase angle for each measurement made for a patient, and
an application program for execution on the processing system, wherein the applications program includes instructions and criteria by which a user can access at least one of the stored time sequence computed impedance and phase angle.

49. A system for detecting the onset of labor; comprising:
a bioimpedance measuring apparatus;
a computer processing system operably coupled to the bioimpedance measuring apparatus: and
wherein the bioimpedance measuring apparatus includes:
a measuring probe being configured and arranged for insertion into a bodily opening, the measuring probe including a plurality or more of electrodes arranged so that ends thereof are spaced from a top surface of the probe,
a signal generator being configured and arranged so as to generate an application voltage and current,
a sensing device for sensing and measuring an electrical characteristic associated with tissue impedance,
wherein the signal generator is operably coupled to certain of the plurality or more electrodes so that when these certain electrodes are in contact with the tissues the applied current flows through a region of the tissues and is dispersed responsive to the impedance of the tissue,
wherein the sensing device is operably coupled to certain of the plurality or more of electrodes so as to sense and measuring a voltage drop associated with the tissue impedance while the voltage and current is being applied to the region of the tissues, and
a computing device being configured and arranged so as to compute an impedance and voltage phase angle using the measured voltage drop and to output the computed impedance and voltage phase angle to said computer system, and
wherein said computer processing system includes:
a database for storing histological information the histological information including clinical/diagnostic information correlated to an impedance and phase angle for a given gestation time, and
an application program for execution on the processing system, wherein the application program includes instructions and criteria for comparing the computed impedance and phase angle to the stored histological information and outputting the clinical/diagnostic information that relates to the computed impedance and phase angle and the gestation time.

* * * * *